United States Patent [19]
Sherwood et al.

[11] Patent Number: 6,165,755
[45] Date of Patent: *Dec. 26, 2000

[54] CHICKEN NEUROPEPTIDE GENE USEFUL FOR IMPROVED POULTRY PRODUCTION

[75] Inventors: Nancy G. M. Sherwood, Victoria; John E. McRory, Vancouver, both of Canada

[73] Assignee: University of Victoria Innovation and Development Corporation, Victoria, Canada

[*] Notice: This patent issued on a continued prosecution application filed under 37 CFR 1.53(d), and is subject to the twenty year patent term provisions of 35 U.S.C. 154(a)(2).

[21] Appl. No.: 08/789,329

[22] Filed: Jan. 23, 1997

[51] Int. Cl.$^7$ ............................ C12N 15/18; C12N 15/63; C12N 15/85; C12N 1/21

[52] U.S. Cl. ...................... 435/69.4; 536/23.51; 435/325; 435/252.3; 435/320.1

[58] Field of Search ................................ 536/23.1, 23.51; 435/325, 252.3, 320.1, 69.4

[56] References Cited

U.S. PATENT DOCUMENTS

| | | | |
|---|---|---|---|
| 5,128,242 | 7/1992 | Arimura et al. | 435/7.21 |
| 5,326,860 | 7/1994 | Onda et al. | 530/324 |
| 5,521,069 | 5/1996 | Onda et al. | 435/69.1 |

FOREIGN PATENT DOCUMENTS

| | | |
|---|---|---|
| 0 404 034 A2 | 12/1990 | European Pat. Off. . |
| WO 94/26897 | 11/1994 | WIPO . |
| WO 96/09064 | 3/1996 | WIPO . |

OTHER PUBLICATIONS

Rudinger In "Peptide Hormones" (Jun. 1976) ed. J.A. Parsons, University Park Press, Baltimore, pp 1–7.
Schoepfer Gene 124 (1993) 83–85.
McRory et al. Society For Neuroscience Abstracts 21 (1995) 1393.
Yasuhara et al., EMBL databank, accession No. A61070 (1992) (XP002068607).
Etches, Robert J., "Transgenic Chickens: Promising Applications for Ontario's Poultry Industry," *Agri–food research in Ontario*, pp. 36–38 (1996).
Sherwood, N.M. and McRory, J.E., "An Avian Gene In The GHRH–PACAP Family," Abstract, VI International Symposium on Avian Endocrinology (Mar. 31–Apr. 5, 1996).
Pain et al., "Long–term in vitro culture and characterisation of avian embryonic stem cells with multiple morphogenetic potentialites," *Development* 122:2339–2348 (1996).
Naito, et al., "Production of Germline Chimeric Chickens, With High Transmission Rate of Donor–Derived Gametes, Produced by Transfer of Primordial Germ Cells," *Molecular Reproduction and Development* 39:153–161 (1994).
Chang, et al., "Simply Method For Isolation of Primordial Germ Cells From Chick Embryos," *Cell Biology International Reports*, vol. 16, No. 9, pp. 853–857 (1992).

Rudman, et al., "Effects of Human Growth Hormone in Men Over 60 Years Old," *The New England Journal of Medicine*, vol. 323, No. 1 (1990).
Perez, F.M., Malamed, S. and Scanes, C.G., "Growth Hormone Secretion from Chicken Adenohypophyseal Cells in Primary Culture: Effects of Human Pancreatic Growth Hormone–Releasing Factor, Thyrotropin–Releasing Hormone, and Somatostatin on Growth Hormone Release," *General and Comparative Endocrinology* 65:408–414 (1987).
Rudman, D., "Growth Hormone, Body Composition, and Aging," *Journal of the American Geriatrics Society*, vol. 33, No. 11 (1985).
Singh and Meyer, "Primordial Germ Cells in Blood Smears from Chick Embryo," *Science*, (1967).
Ogi et al., "Molecular Cloning and Characterization of cDNA for the Precursor of Rat Pituitary Adenylate Cyclase Activating Polypeptide (PACAP)", *Biochem. and Biophys. Research Comm.*, vol. 173, 3:1271 (1990).
Kimura et al., "A Novel Peptide which Stimulates Adenylate Cyclase: Molecular Cloning and Characterization of the Ovine and Human cDNAs," *Biochem. and Biophys. Res. Comm.* vol. 166, 1:81 (1990).
Rivier et al., "Characterization of a Growth Hormone–Releasing Factor from a Human Pancreatic Islet Tumor," *Nature* 300:276 (1982).
Guillemin et al., "Growth Hormone–Releasing Factor from a Human Panacreatic Tumor that Caused Acoromegaly," *Science* 218:585 (1982).
Spiess et al., "Characterization of Rat Hypothalamic Growth Hormone–Releasing Factor," *Nature* 303:532 (1983).
Barinaga et al., "Transcriptional Regulation of Growth Hormone Gene Expression by Growth Hormone–Releasing Factor," *Nature* 306:84 (1983).
Frawley, L.S. and Hoeffle, J.P., "Hypothalamic Peptides Affect the Ratios of GH and PRL Cells: Role of Cell Division," *Peptides* 9:825 (1988).
Gick et al., "Growth Hormone–Releasing Factr Regulates Growth Hormone mRNA in Primary Cultures of Rat Pitituary Cells," *PNAS* (USA) 81:1553 (1984).
Guillemin, R., "Hypothalamic Control of Pituitary Functions. The Growth Hormone Release Factor," Liverpool University Press, Liverpool, U.K., pp. 1–73 (1986).
Froham. L.A. and Jansson, J.O., "Growth Hormone–Releasing Hormone," *Endocr. Rev.* 7:223 (1986).
Vaughan et al., "Isolation and Characterization of Hypothalamic Growth–Hormone Releasing Factor from Common Carp, Cyprinus Carpio," *Neuroendocr.* 56:539 (1992).
Mayo et al., PNAS 82:63–67 (1985).
Parker et al., *Gen. Comp. Endocrinol.* 79:95–102 (1990).
Froham et al., *Mol. Endocrinol.* 3:1529–1536 (1989).
OhKubo et al., *DNA & Cell Biology* 11:21–30 (1992).
Ackland et al., *Peptides* 10:15–19 (1989).
Friedenreich et al., *Nucl. Acids Res.* 18:3299–3305 (1990).

*Primary Examiner*—Gary L. Kunz
*Assistant Examiner*—Robert C. Hayes
*Attorney, Agent, or Firm*—Klarquist Sparkman Campbell Leigh & Whinston, LLP

[57] ABSTRACT

The nucleotide sequence of a gene encoding two chicken neuropeptides is disclosed, together with the amino acid sequences of these neuropeptides. The neuropeptides are useful to modify the body composition of poultry.

12 Claims, 2 Drawing Sheets

```
2881 gtgactccgtgctgatgctgtgcttggggctttcttgctaccaagtgtaagtgctatgtgagttgcagcttcgcatttgc 2960
          CAAT-box                            TATAA-box
2961 agactcctatgggcaattttagaaaaaggagttaattaatataaatttggggtgtttctctgaagatatttcactcca 3040

3041 cagtgaaaacagatttcttctaagcctcagGCGAATATTGACAGCCCCCCTTTTTTTTCCTTTATTTGTCGAGTCGATTC 3120
3121 CCTAACCACCCAACAACTCTCTGCGCTTCTGCGCCTTCTTCATCCTTGCCCAGCGGAAAAGCCGGGAGCCCTTTGACTCT 3200
3201 TTCGGCCGCAACTTGGGGAGATAGCTCTATTTTTCCCCCCTCCTCTCTGGGGTTTTTCTCCTTTTTCCTCTCTCCCTTTC 3280
3281 CCTTCCGCAGCCACACGCTCTCAGTGCCGGGTGTCACAgtgtgtaaatcaagacttgaggatcaccctaaggtgtatgcc 3360
3361 ttgttcttgtttcagtagtacagagtgaatgaaaaaccactggataagcatgttgagttagcttctctgatttgggtgta 3440
3441 ggagtgacaagaatttgctctgagacacagGTTTC ATG AGT GGC AAT GTG TAT AAA ACG CTC TTA ACC 3508
   1                               M   S   G   N   V   Y   K   T   L   L   T   11

3509 CTC CTG GTC TAT GGA TTA ATA ATG CAT TGC AAC GTC TAC TGC TCA CCC GAC CGT TGG ACT 3568
  12  L   L   V   Y   G   L   I   M   H   C   N   V   Y   C   S   P   D   R   W   T   31

3569 CCA GTA CCC GGC GCT AAG gtgagtctgtcagtgcaatatgctactctcacatcaggctctgtgtcacaagtcat 3642
  32  P   V   P   G   A   K                                                          37
3643 ctgccaatctatcagtgctgttaagtggaattactgagtaggtgcttggcccaccaaggctgagaatccagctgcagtgg 3722
3723 atcagcccatctaccccctgcacacacgtgtggattcaccccatccctgccaacccctgccaccccatgctgccccacac 3802
                               ------------INTRON 2------------
4763 aggaatgactcctcctttgctactcttatttccactgtatgggttaagaagactcgtcacgctgggctgagcactggag 4842
4843 cgagctcgctccgtcccgcacggtcccgcggcgggacgggctggggacgtccggctgagcccgcccgtgcttaccgca 4922
4923 g CTG GAG GAG GAG GTA TAC GAC GAG GAC GGG AAT ACC CTA CAG GAC TTC GCA CTA CGA 4980
  38  L   E   E   E   V   Y   D   E   D   G   N   T   L   Q   D   F   A   L   R   56

4981 GCA GGA GCC CCT GGG GGT GGC GGG CCG CGC CCG CGC TGG GGC AGG TGT ACG GCG CTG TAC 5040
  57  A   G   A   P   G   G   G   G   P   R   P   R   W   G   R   C   T   A   L   Y   76

5041 TAC CCG CCG GGA AAG AG gtgacagaggggcgccggatagggccggggggggaggggggggaatgggaaacctaag 5114
  77  Y   P   P   G   K   R                                                            82
5115 ggccccggggggaggccgggaaatatcgtaattccgccccacctggctgcgcgagcgggggaggggggtggggagggag 5194
5195 ggcgcctcggggatgggcgctgacgggccgtgccccgcag G CAC GCC GAT GGG ATC TTC AGC AAA GCC 5263
  83                                           A   D   G   I   F   S   K   A   91

5264 TAC AGG AAA CTC CTG GGC CAG CTG TCC GCA AGA AAT TAC CTG CAC TCC CTG ATG GCC AAG 5323
  92  Y   R   K   L   L   G   Q   L   S   A   R   N   Y   L   H   S   L   M   A   K   111

5324 CGG GTC GG gtaagggctgcggcgggacgggagcgaacaaagcgcggcgcgcggcggccggggcggggcggcccattc 5400
 112  R   V   G                                                                       114
5401 tcccgcggtgctctgccggaacgagagaggcggccgcacccgggctcggcgtccctcccgcggggcagcccgggtgg 5480
                        ------------INTRON 4------------       +          ++
5641 cgggttgggtcgggccgggagggcccctcctgatggttgtgtccttctcggtgctttgcag C GGT GCC AGC AGC 5715
 115                                                                G   A   S   S   118

5716 GGC CTG GGG GAC GAG GCG GAA CCG CTC AGC AAG CGC CAC ATA GAC GGC ATC TTC ACG GAC 5775
 119  G   L   G   D   E   A   E   P   L   S   K   R   H   I   D   G   I   F   T   D   138

5776 AGC TAC AGC CGC TAC CGG AAA CAA ATG GCT GTC AAG AAA TAC TTA GCG GCC GTC CTG GGG 5835
 139  S   Y   S   R   Y   R   K   Q   M   A   V   K   K   Y   L   A   A   V   L   G   158

5836 AAA AGG TAT AAA CAA AGA GTT AAA AAC AAA GGA CGC CGA GTA GCG TAT TTG TAG gatgagca 5897
 159  K   R   Y   K   Q   R   V   K   N   K   G   R   R   V   A   Y   L   *       176
5898 accgccgctgccgtgcgtagtcctgagagagagagagagagagagagattgagagagagagagagagagagagagaga 5977
5978 cccaacccacccccaacccaaacaaaagtcatttccaaagtgacggaacgaccgccgctcccgtgttccccaaacatgtatt 6057
6058 tatgtataagtaagccattaaatgaataatattttgataataatatggttttcttttgtacgaaagcacagatctactttt 6137
6138 gtggaccaatccttgagttatatatgagatagaatatatatatataatactgctactaaagagcgattcttcataccaag 6217
6218 ctgcaccaggacgagagttcgcctgagctgttagttttttatagaaaacaaatagacgaaaaaaaaaaaaaagacaatcac 6297
6298 cgcttccaacagcgctcctatttttgtaacggaaacgaaaagggcactgttttattgccacggggggcgaacacctcagt 6377
6378 tctcaccgtgtgcgctgtgataggaggggctcacgcagcaggggtcccccggcctcgatctctctctctatttcccca 6457
6458 cccccccttttttttttttcccttgattccggtcctatccgtatcagtcctcctcagagcgatgag            6525
```

Figure 2

SEQUENCE LISTING (1) GENERAL INFORMATION:

(iii) NUMBER OF SEQUENCES: 20

(2) INFORMATION FOR SEQ ID NO: 1:

(i) SEQUENCE CHARACTERISTICS:
      (A) LENGTH: 6529 bp
      (B) TYPE: nucleic acid
      (C) STRANDEDNESS: double
      (D) TOPOLOGY: linear (xi) SEQUENCE DESCRIPTION: SEQ ID NO:1:

```
TTTTTCCCAC AGTAACAATT CTGGTTGAAA TAATAAAAAG GATTATTTTT TGGATATGTT      60

AAATACTGAA ATTTTGATTT TTGGACTCTG GTGTAATTTT TTTTCCTGGG GGTTCCTTGC     120

TACCAAGTGT AAGTATATTA TTGACTTTTG AATCCGATGG GCTTTTAGAA AAAGGAGTTA     180

ATTTATATAT TTGGGGTGTT TCTCTGAGAT ATTTCACTCC ATGAAAACAG ATTTCTTCTA     240

AGCCTCAGCA AGACTTGAGA TCACCCTAAA ATGTATGCAT TGTTCTTGTT TTCCATAAGC     300

ATCCTTGAGT TAGCCTTCTC TGATGTTTAA ATGTAGGGAG GTGACCAGAA TTTGCTCTGA     360
```

```
GACACAATGA CAAGGAAGGT ATGAGCACAG AATTACAGAA AGGGAAAAAA TACATATTCT      420

ACTCAGATAA AATAAAGCTG TTGTCAATAA CATGATTTAT TCAAACTCCT CATCTATGGG      480

AAGTAAGTAA CTCTGTTCTG AATATATCTA CTGTCTATAA CTCGACAGAT CAGTTCTGCA      540

GTTCGTGTTC TGGACCAGGG ATTGCGTGGG GTGCACTGGG CACAACCACA TCTTTGATTT      600

CTTTCTTCAA ATTCTCAGTG TAGAATGTTT TTATATTACC TCAAAAGCTT GAGATACAAG      660

GTAAATACAG GGGTATAGGT TTAAAGTTCT GTGTAAGTGT GGGGAAAATA TCTCCACATC      720

ACAGAGTTTG GAGAAAAGGC AATCTGCATT TGCTGATGTG CACATACAAA TTTCTATGGG      780

TTCTTCATGC TACATTAAAA GCTTCACAAG GAATCTTTCC CCAACTTCCA GCGTTGATTA      840

GTGAACAGCG CTATTAGTCA TTACACTCAA TATACTTGGT GTCCTTCCTT GATTTTCCTG      900

AAGAAGCAGC AGTAGGGAGA GCTGAATCAC GAGTTTTCCT CATATTTTTC TTAATGAAAA      960

ATCATTTGCA CTGCTGTTCT GGAACACAGC ACCAGGTAAT GTCAACACAT TAGAAAGATG     1020

ACAAAAGTTC CCAATCACGG GTCTCGAGTC AGCTCCCTTT AGTGAGGTTA ATTGAGCTTC     1080

CAATTCGAAT ATAGTGAGTC GTATTACGCG CGCTCACTGG CCGTCGTTTT ACAACGTCGT     1140

GACTGGGAAA CCCTGGCGTT ACCCAACTTA ATCGCCTTGC AGCACATCCC CCTTTCGCCA     1200

GCTGGCGTAT AGCGAAGAGG CCCGCACCGA TCGCCCAACC CAACAGTTGC GCAGCCTGAA     1260

TGGCGAATGG GACGCGCCCT GTAGCGCTCA TTAAGCGCGG CGGGAAGCTC TAAATCGGGG     1320

GGCTCCTTTA GGTTCCGATT AGTGCTTTAC GGCACCTCGA CCCCAAAAAA ACTTGATTAG     1380

GGTGATGGTT CACGTAGTGG CCTACGCCCT GATAGACGGT TTTTTCGCC CTTTGACGTT     1440

GGAGTCCACG TTCTTTAATA GTGGACTCTT GTTCCAAACT GGAACAACAC TCAACCCTAT     1500

CTCGGTCTAT TCTTTTGATT TATAAGGGAT TTTGCCGATT TCGGCCTATT GGTTAAAAAA     1560

TGAGCTGATT TAACAAAAAT TTAACGCGAA TTTTAACAAA ATATTAACGC TTACAATTTA     1620

GGTGGCACTT TTCGGGGAAA TGTGCGCGGG GCCCCTATTG TTTATTTTTC TAATACATTC     1680

AAATATGTAT CCGCTCATGA GACAATAACC CTGATAAATG CTTCAGTAAT ATTGCATAAT     1740

TTACAATGGC GAAGAAAACT ATACATCCCC CCCCAGACAA TCTAGGGTGT CTCTCTACCT     1800

CCAAGAGATC GATGTCAAGA GATCGCCTAG AACATCGTAT TATCTCTTTC CCGGAGAGGC     1860

AAGTATACAA GAAGAATTAA CTCAATGTGA AGAATACATC TTAGAGGGAT TATACGATGA     1920

CTCCTACCCT CTGATCTGGG CTTCTTCCTA TCGCGCACTC TGAGAGAAGC AACCGAGAAT     1980

TCAGCCCTTT ATAAGAGTGT GATTTTAGCC AAAATGAATT CCATCCCACC CATCCCAAAA     2040

GTCGGATACT GTGGGTTCAG TACCGTGCAT CGATCGATCG ATGGAGCATG CATCGATGCT     2100

AGCATGCATG CTAGCTAGCT ATTCTTTATT TTTTTTTTTG TATGCTAGAT AAAGCTTTCG     2160

GTTTGGATTT TACGACGTCT TGCATACGCA CTGAACTTGA CATTGACATC TCTTTGCACA     2220

CCTAAACTAA AAATAATTAA GCCCATTACT CATCCTCAGA GAACCAAGGT AATCAAGGAG     2280

TCTTTGCAAC TGAGCAAAAG CTGTCCTTCA GAAGGAATCT TTCCCCAACT TCCAGCGTTG     2340

ATTAGTGAAC AGCGCTATTA GTCATTACAC TCAATATACT TGGTGTCCTT CCTTGATTTT     2400

CCTGGGGGAA GAAGCAGGAG TAGGGAGAA CTGAATCACG AGTTTTCCTC ATATTTTTCT     2460

TAATGAAAAA GCTCATTAAT GGATGCTGTT CTGGAACACA GGACCAGGTA ATGTCAAAAC     2520

ATTAAAAAGA TGACAAAAGT TCCCAAGGAC GGATCTCGAG TCGACTCACA ACCAGAGGTT     2580

GCCAGGACAT TGCAGGACTG AACTTTCTCT TTCAACCCTC CAATCTATTT TGAGCTCTCC     2640

AGAGGAAATG GGATTTGTCC ACAGTAACCA CTGTGGCTGA GATAATAAAC TGCATTACTC     2700
```

```
TCTGGATATG TTTAAAATAC TGAGACTTTA ATATGATTTT TGCATCTCAG TGTAATTTCT      2760

TTTCCGATGC TAGCATCGAT GCTAGCTGGG CGGGTTATCA TGCCCAACGT CGTAGCTGTG      2820

ATAAAAAAAA ATGACGTCTG TGCTGTAGCT GATCGATGCA TGCATGAATA AAAAAAGTGT      2880

GTGTGTGACT CCGTGCTGAT GCTGTGCTTG GGGCTTTCTT GCTACCAAGT GTAAGTGCTA      2940

TGTGAGTTGC AGCTTCGCAT TTGCAGACTC CTATGGGCAA TTTTTAGAAA AAGGAGTTAA      3000

TTTAATATAA ATTTGGGGTG TTTCTCTGAA GATATTTCAC TCCACAGTGA AAACAGATTT      3060

CTTCTAAGCC TCAGGCGAAT ATTGACAGCC CCCCTTTTTT TTCCTTTATT TGTCGAGTCG      3120

ATTCCCTAAC CACCCAACAA CTCTCTGCGC TTCTGCGCCT TCTTCATCCT TGCCCAGCGG      3180

AAAAGCCGGG AGCCCTTTGA CTCTTTCGGC CGCAACTTGG GGAGATAGCT CTATTTTTCC      3240

CCCCTCCTCT CTGGGGTTTT TCTCCTTTTT CCTCTCTCCC TTTCCCTTCC GCAGCCACAC      3300

GCTCTCAGTG CCGGGTGTCA CAGTGTGTAA ATCAAGACTT GAGGATCACC CTAAGGTGTA      3360

TGCCTTGTTC TTGTTTCAGT AGTACAGAGT GAATGAAAAA CCACTGGATA AGCATGTTGA      3420

GTTAGCTTCT CTGATTTGGG TGTAGGAGTG ACAAGAATTT GCTCTGAGAC ACAGGTTTC      3479

ATG AGT GGC AAT GTG TAT AAA ACG CTC TTA ACC CTC CTG GTC TAT GGA TTA  3530
Met Ser Gly Asn Val Tyr Lys Thr Leu Leu Thr Leu Leu Val Tyr Gly Leu
1                 5                  10                  15

ATA ATG CAT TGC AAC GTC TAC TGC TCA CCC GAC CGT TGG ACT CCA GTA CCC  3581
Ile Met His Cys Asn Val Tyr Cys Ser Pro Asp Arg Trp Thr Pro Val Pro
        20                  25                  30

GGC GCT AAG GTGAGTCTGT CAGTGCAATA TGCTACTCTC ACATCAGGCT CTGTGTCACA   3640
Gly Ala Lys
35

AGTCATCTGC CAATCTATCA GTGCTGTTAA GTGGAATTAC TGAGTAGGTG CTTGGCCCAC      3700

CAAGGCTGAG AATCCAGCTG CAGTGGATCA GCCCATCTAC CCCCTGCACA CACGTGTGGA      3760

TTCACCCCAT CCCCTGCCAA CCCTGCCACC CCATGCTGCC CCACACAGTC CCTATAGGGA      3820

TGAGGCTCTC CCACCAGGGG ACTGTGCTGC CACCATCCGA CACTCCTCTA GCAACCAAGC      3880

AACCAACCAA ATTGGTGTTT TGTAATAGGC TGCATGCTGT TTTGTAATAG GAAATATAGA      3940

TGATTCTACT TTATTCTCCC TGGCTCCTGC AACGATAAGA ATGTTCTAAT TCATTATTAA      4000

TTTGTTCCTT CTATTTCTGG TAATTCTAAA CTATGGATAA CCTCAGTGAT GCCATTAGCA      4060

ATACCTCGAG GACTACGAGA TGGGGTTTAC GTTTCTGGAC ATGGGTCGT GGAGGCAGCC       4120

CCTCTGGCCA TAAGGTGGTT CCCTAAACCC TGACACATTT GGGACATAAC TGGTACTTGC      4180

CATTCACACT GGGTTACAGT GTTGTGACAA CAACCTGGA GCACAGAGAA ATCGTGGCTA       4240

GTTATTTGTC TGGTGTAAAT GATTGTAGCT CAGCAGCACT CCGTGAAACT TGCTTATTCC      4300

ATCTGTTTAT GGATTTACTC TCCACTGAGC ACAAATGGAA ATGAGGGTGG GAGCAGGGCC      4360

TAGGGTCTTC TGCCAGCACC AGGGGCTGAC TCCTCCCATG GGCCTGCCAA GGCCTGCAGT      4420

GACATTCTGC AAGCTAGCTG GTGTTAGTGT AGAGGAGGGG CCATGGAACA TTACATCTCC      4480

AAAAGGTACT TTTTCGATCT TGGATTGCAC TTTCATAATT TATTTCTCTA TTCAAATGAT      4540

TGATTGAAGA ACAGTTGTTA AAAAATCTAG GGAAATGATA TTTTTATTCT TCTGTAAAAT      4600

ACAAACTTAT CTGGGTGAAA AATGGGAGAT TACAAGTATA TCTGTTGGTC TCTGGAGGAA      4660

ATTAGCTGCA ACCCGTGTGG CATGATGGCA CCTCCTTGTG CAGCCAAGCC TTCTGTTAGG      4720

CTTTCCGTTC ATCTAGAAAG TGCTCTCCTT GCCTTTGTGT TTTGATAGGA ATGACTCCTC      4780

CTTTGCTACT CTTATTTCCA CTGTATGGGG TTAAGAAGAC TCGTCACGCT GGGCTGAGCA      4840

CTGGAGCGAG CTCGCTCCGT CCCGCACGGT CCCGCGGCGG GGACGGGGCT GGGGACGTCC      4900
```

```
GGCTGAGCCC GCCCGTGCTT ACCGCAG CTG GAG GAG GAG GTA TAC GAC GAG GAC    4954
                            Leu Glu Glu Glu Val Tyr Asp Glu Asp
                                     40                  45

GGG AAT ACC CTA CAG GAC TTC GCA CTA CGA GCA GGA GCC CCT GGG GGT GGC  5005
Gly Asn Thr Leu Gln Asp Phe Ala Leu Arg Ala Gly Ala Pro Gly Gly Gly
                50                  55                  60

GGG CCG CGC CCG CGC TGG GGC AGG TGT ACG GCG CTG TAC TAC CCG CCG GGA  5056
Gly Pro Arg Pro Arg Trp Gly Arg Cys Thr Ala Leu Tyr Tyr Pro Pro Gly
    65                  70                  75                  80

AAG AG GTGACAGAG GGGCGCCGGA TAGGGCCGGG GGGGGAGGGG GGGAATGGGA         5110
Lys Arg

AACCTAAGGG CCCCCGGGGG AGGCCGGGAA ATATCGTAAT TCCGCCCCAC CTGGGCTGCG    5170

CGAGCGGGGG AGGGGGGTGG GGAGGGAGGG CGCCTCGGGG ATGGGCGCTG ACGGGCCGTG    5230

CCCCGGCAG G CAC GCC GAT GGG ATC TTC AGC AAA GCC TAC AGG AAA CTC CTG  5282
            His Ala Asp Gly Ile Phe Ser Lys Ala Tyr Arg Lys Leu Leu
                         85                  90                  95

GGC CAG CTG TCC GCA AGA AAT TAC CTG CAC TCC CTG ATG GCC AAG CGG GTC  5333
Gly Gln Leu Ser Ala Arg Asn Tyr Leu His Ser Leu Met Ala Lys Arg Val
                100                 105                 110

GG GTAAG GGCTGCGGCG GGACGGGAGC GAACAAAGCG CGGCGCGCGG CGGCCGGGGC      5390
Gly

GGGGCGGCCC ATTCTCCCCG CGGTGCTCTG CCGGAACGAG AGAGGCGGCC GCACCCGGGG    5450

CTCGGCGTCC CTCCCGCGGG GCAGCCCCGG GTGGTGCCAT CGGAGCGAAC CCCCCCCGGG    5510

AACGCGATGC ATAATGCATG GGGGGGGGGG GGGGAGACGT CTCGCTCCGG CCCGGCCCCG    5570

CCCTTTGTCT GCCGGGAGAT GCGGGGCCGG GGCGGGGGTT AGGGCCGGGG TTGGGGTTGG    5630

GGTTGGGTTA GGGCCGGGTT GGGTCGGGCC CGGGAGGGCC CCTCCTGATG GTTGTGTCCT    5690

TCTCGGTGCT TTGCAG C GGT GCC AGC AGC GGC CTG GGG GAC GAG GCG GAA CCG  5743
                    Gly Ala Ser Ser Gly Leu Gly Asp Glu Ala Glu Pro
                    115                 120                 125

CTC AGC AAG CGC CAC ATA GAC GGC ATC TTC ACG GAC AGC TAC AGC CGC TAC  5794
Leu Ser Lys Arg His Ile Asp Gly Ile Phe Thr Asp Ser Tyr Ser Arg Tyr
                130                 135                 140

CGG AAA CAA ATG GCT GTC AAG AAA TAC TTA GCG GCC GTC CTG GGG AAA AGG  5845
Arg Lys Gln Met Ala Val Lys Lys Tyr Leu Ala Ala Val Leu Gly Lys Arg
    145                 150                 155                 160

TAT AAA CAA AGA GTT AAA AAC AAA GGA CGC CGA GTA GCG TAT TTG TAG      5893
Tyr Lys Gln Arg Val Lys Asn Lys Gly Arg Arg Val Ala Tyr Leu
                165                 170                 175

GATGAGC AACCGCCGCT GCCGTGCGTA GTCCTGAGAG AGAGAGAGAG AGAGAGAG         5950

AGATTGAGAG AGAGAGAGAG AGAGAGAGAG ACCCAACCAC CCCAACCCAA ACAAAAGTCA    6010

TTTCCAAAGT GACGGAACGA CCGCCGCTCC CGTGTTCCCC AAACATGTAT TTATGTATAA    6070

GTAAGCCATT AAATGAATAA TATTTTGATA ATAAATATGGT TTTCTTTTGT ACGAAAGCAC   6130

AGATCTACTT TGTGGACCAA TCCTTGAGTT ATATATGAGA TAGAATATAT ATATATAATA    6190

CTGCTACTAA AGAGCGATTC TTCATACCAA GCTGCACCAG GACGAGAGTT CGCCTGAGCT    6250

GTTAGTTTTT ATAGAAAACA AATAGACGAA AAAAAAAAA AAGACAATCA CCGCTTCCAA     6310

CAGCGCTCCT ATTTTTGTAA CGGAAACGAA AAGGGCACTG TTTTTATTGC CACGGGGGCG    6370

AACACCTCAG TTCTCACCGT GTGCGCTGTG ATAGGGAGGG CTCACGCAGC AGGGGTCCCC    6430

CCGGCCTCGA TCTCTCTCTC TATTTCCCCC ACCCCCCCCT TTTTTTTTT TCCCTTTGAT     6490

TCCGGTCCTA TCCGTATCAG TCCTCCTCAG AGCGATGAG                           6529
```

(2) INFORMATION FOR SEQ ID NO: 2:

(i) SEQUENCE CHARACTERISTICS:
        (A) LENGTH: 1088 bp
        (B) TYPE: nucleic acid
        (C) STRANDEDNESS: double
        (D) TOPOLOGY: linear (xi) SEQUENCE DESCRIPTION: SEQ ID NO:2:

```
GCGAATATTG ACAGCCCCCC TTTTTTTTCC TTTATTTGTC GAGTCGATTC CCTAACCACC     60

CAACAACTCT CTGCGCTTCT GCGCCTTCTT CATCCTTGCC CAGCGGAAAA GCCGGGAGCC    120

CTTTGACTCT TTCGGCCGCA ACTTGGGGAG ATAGCTCTAT TTTTCCCCCC TCCTCTCTGG    180

GGTTTTTCTC CTTTTTCCTC TCTCCCTTTC CCTTCCGCAG CCACACGCTC TCAGTGCCGG    240

GTGTCACAGT TTC ATG AGT GGC AAT GTG TAT AAA ACG CTC TTA ACC CTC CTG    292
        Met Ser Gly Asn Val Tyr Lys Thr Leu Leu Thr Leu Leu
         1               5                  10

GTC TAT GGA TTA ATA ATG CAT TGC AAC GTC TAC TGC TCA CCC GAC CGT TGG    343
Val Tyr Gly Leu Ile Met His Cys Asn Val Tyr Cys Ser Pro Asp Arg Trp
        15              20                  25              30

ACT CCA GTA CCC GGC GCT AAG CTG GAG GAG GAG GTA TAC GAC GAG GAC GGG    394
Thr Pro Val Pro Gly Ala Lys Leu Glu Glu Glu Val Tyr Asp Glu Asp Gly
                35              40                  45

AAT ACC CTA CAG GAC TTC GCA CTA CGA GCA GGA GCC CCT GGG GGT GGC GGG    445
Asn Thr Leu Gln Asp Phe Ala Leu Arg Ala Gly Ala Pro Gly Gly Gly Gly
        50              55                  60

CCG CGC CCG CGC TGG GGC AGG TGT ACG GCG CTG TAC TAC CCG CCG GGA AAG    496
Pro Arg Pro Arg Trp Gly Arg Cys Thr Ala Leu Tyr Tyr Pro Pro Gly Lys
65              70                  75              80

AGG CAC GCC GAT GGG ATC TTC AGC AAA GCC TAC AGG AAA CTC CTG GGC CAG    547
Arg His Ala Asp Gly Ile Phe Ser Lys Ala Tyr Arg Lys Leu Leu Gly Gln
        85              90                  95

CTG TCC GCA AGA AAT TAC CTG CAC TCC CTG ATG GCC AAG CGG GTC GGC GGT    598
Leu Ser Ala Arg Asn Tyr Leu His Ser Leu Met Ala Lys Arg Val Gly Gly
        100             105                 110             115

GCC AGC AGC GGC CTG GGG GAC GAG GCG GAA CCG CTC AGC AAG CGC CAC ATA    649
Ala Ser Ser Gly Leu Gly Asp Glu Ala Glu Pro Leu Ser Lys Arg His Ile
                120             125                 130

GAC GGC ATC TTC ACG GAC AGC TAC AGC CGC TAC CGG AAA CAA ATG GCT GTC    700
Asp Gly Ile Phe Thr Asp Ser Tyr Ser Arg Tyr Arg Lys Gln Met Ala Val
        135             140                 145

AAG AAA TAC TTA GCG GCC GTC CTG GGG AAA AGG TAT AAA CAA AGA GTT AAA    751
Lys Lys Tyr Leu Ala Ala Val Leu Gly Lys Arg Tyr Lys Gln Arg Val Lys
150             155                 160             165

AAC AAA GGA CGC CGA GTA GCG TAT TTG TAG
Asn Lys Gly Arg Arg Val Ala Tyr Leu
        170             175

GATGAGCAA CCGCCGCTGC CGTGCGTAGT    810

CCTGAGAGAG AGAGAGAGAG AGAGAGAGAG ATTGAGAGAG AGAGAGAGAG AGAGAGAGAC    870

CCAACCACCC CAACCCAAAC AAAAGTCATT TCCAAAGTGA CGGAACGACC GCCGCTCCCG    930

TGTTCCCCAA ACATGTATTT ATGTATAAGT AAGCCATTAA ATGAATAATA TTTTGATAAT    990

AATATGGTTT TCTTTTGTAC GAAAGCACAG ATCTACTTTG TGGACCAATC CTTGAGTTAT   1050

ATATGAGATA GAATATATAT ATATAATACT GCTACTAA                          1088
```

(2) INFORMATION FOR SEQ ID NO:3:

(i) SEQUENCE CHARACTERISTICS:

(A) LENGTH: 175 aa
        (B) TYPE: amino acid
        (C) STRANDEDNESS: single
        (D) TOPOLOGY: linear (xi) SEQUENCE DESCRIPTION: SEQ ID NO:3:

Met Ser Gly Asn Val Tyr Lys Thr Leu Leu Thr Leu Val Tyr Gly
1               5                  10                 15

Leu Ile Met His Cys Asn Val Tyr Cys Ser Pro Asp Arg Trp Thr Pro
                20                  25                  30

Val Pro Gly Ala Lys Leu Glu Glu Val Tyr Asp Glu Asp Gly Asn
            35                  40                  45

Thr Leu Gln Asp Phe Ala Leu Arg Ala Gly Ala Pro Gly Gly Gly Gly
        50                  55                  60

Pro Arg Pro Arg Trp Gly Arg Cys Thr Ala Leu Tyr Tyr Pro Pro Gly
65                  70                  75                  80

Lys Arg His Ala Asp Gly Ile Phe Ser Lys Ala Tyr Arg Lys Leu Leu
                85                  90                  95

Gly Gln Leu Ser Ala Arg Asn Tyr Leu His Ser Leu Met Ala Lys Arg
            100                 105                 110

Val Gly Gly Ala Ser Ser Gly Leu Gly Asp Glu Ala Glu Pro Leu Ser
        115                 120                 125

Lys Arg His Ile Asp Gly Ile Phe Thr Asp Ser Tyr Ser Arg Tyr Arg
130                 135                 140

Lys Gln Met Ala Val Lys Lys Tyr Leu Ala Ala Val Leu Gly Lys Arg
145                 150                 155                 160

Tyr Lys Gln Arg Val Lys Asn Lys Gly Arg Arg Val Ala Tyr Leu
                165                 170                 175

(2) INFORMATION FOR SEQ ID NO:4:

(i) SEQUENCE CHARACTERISTICS:
        (A) LENGTH: 46 aa
        (B) TYPE: amino acid
        (C) STRANDEDNESS: single
        (D) TOPOLOGY: linear (xi) SEQUENCE DESCRIPTION: SEQ ID NO:4:

His Ala Asp Gly Ile Phe Ser Lys Ala Tyr Arg Lys Leu Leu Gly Gln
1               5                  10                  15

Leu Ser Ala Arg Asn Tyr Leu His Ser Leu Met Ala Lys Arg Val Gly
                20                  25                  30

Gly Ala Ser Ser Gly Leu Gly Asp Glu Ala Glu Pro Leu Ser
            35                  40                  45

(2) INFORMATION FOR SEQ ID NO:5:

(i) SEQUENCE CHARACTERISTICS:
        (A) LENGTH: 38 aa
        (B) TYPE: amino acid
        (C) STRANDEDNESS: single
        (D) TOPOLOGY: linear (xi) SEQUENCE DESCRIPTION: SEQ ID NO: 5:

His Ile Asp Gly Ile Phe Thr Asp Ser Tyr Ser Arg Tyr Arg Lys Gln
1               5                  10                  15

Met Ala Val Lys Lys Tyr Leu Ala Ala Val Leu Gly Lys Arg Tyr Lys
                20                  25                  30

Gln Arg Val Lys Asn Lys
            35

(2) INFORMATION FOR SEQ ID NO:6:

(i) SEQUENCE CHARACTERISTICS:
        (A) LENGTH: 1079 bp
        (B) TYPE: nucleic acid
        (C) STRANDEDNESS: double
        (D) TOPOLOGY: linear (xi) SEQUENCE DESCRIPTION: SEQ ID NO:6:

```
GCGAATATTG ACAGCCCCCC TTTTTTTTCC TTTATTTGTC GAGTCGATTC CCTAACCACC     60

CAACAACTCT CTGCGCTTCT GCGCCTTCTT CATCCTTGCC CAGCGGAAAA GCCGGGAGCC    120

CTTTGACTCT TTCGGCCGCA ACTTGGGGAG ATAGCTCTAT TTTTCCCCCC TCCTCTCTGG    180

GGTTTTTCTC CTTTTTCCTC TCTCCCTTTC CCTTCCGCAG CCACACGCTC TCAGTGCCGG    240

GTGTCACAGT TTC ATG AGT GGC AAT GTG TAT AAA ACG CTC TTA ACC CTC CTG   292
        Met Ser Gly Asn Val Tyr Lys Thr Leu Leu Thr Leu Leu
         1               5                  10

GTC TAT GGA TTA ATA ATG CAT TGC AAC GTC TAC TGC TCA CCC GAC CGT TGG   343
Val Tyr Gly Leu Ile Met His Cys Asn Val Tyr Cys Ser Pro Asp Arg Trp
     15                  20                  25                  30

ACT CCA GTA CCC GGC GCT AAG CTG GAG GAG GAG GTA TAC GAC GAG GAC GGG   394
Thr Pro Val Pro Gly Ala Lys Leu Glu Glu Glu Val Tyr Asp Glu Asp Gly
                 35                  40                  45

AAT ACC CTA CAG GAC TTC GCA CTA CGA GCA GGA GCC CCT GGG GGT GGC GGG   445
Asn Thr Leu Gln Asp Phe Ala Leu Arg Ala Gly Ala Pro Gly Gly Gly Gly
             50                  55                  60

CCG CGC CCG CGC TGG GGC AGG TGT ACG GCG CTG TAC TAC CCG CCG GGA AAG   496
Pro Arg Pro Arg Trp Gly Arg Cys Thr Ala Leu Tyr Tyr Pro Pro Gly Lys
65                  70                  75                  80

AGG CAC GCC GAT GGG ATC TTC AGC AAA GCC TAC AGG AAA CTC CTG GGC CAG   547
Arg His Ala Asp Gly Ile Phe Ser Lys Ala Tyr Arg Lys Leu Leu Gly Gln
                 85                  90                  95

CTG TCC GCA AGA AAT TAC CTG CAC TCC CTG ATG GCC AAG CGG GTC GGC AGC   598
Gln Leu Ser Ala Arg Asn Tyr Leu His Ser Leu Met Ala Lys Arg Gly Ser
            100                 105                 110                 115

GGC CTG GGG GAC GAG GCG GAA CCG CTC AGC AAG CGC CAC ATA GAC GGC ATC   649
Gly Leu Gly Asp Glu Ala Glu Pro Leu Ser Lys Arg His Ile Asp Gly Ile
                120                 125                 130

TTC ACG GAC AGC TAC AGC CGC TAC CGG AAA CAA ATG GCT GTC AAG AAA TAC   700
Phe Thr Asp Ser Tyr Ser Arg Tyr Arg Lys Gln Met Ala Val Lys Lys Tyr
            135                 140                 145

TTA GCG GCC GTC CTG GGG AAA AGG TAT AAA CAA AGA GTT AAA AAC AAA GGA   751
Leu Ala Ala Val Leu Gly Lys Arg Tyr Lys Gln Arg Val Lys Asn Lys Gly
150                 155                 160                 165

CGC CGA GTA GCG TAT TTG TAG GATGAGCA
Arg Arg Val Ala Tyr Leu
                170

ACCGCCGCTG CCGTGCGTAG TCCTGAGAGA  810

GAGAGAGAGA GAGAGAGAGA GATTGAGAGA GAGAGAGAGA GAGAGAGAGA CCCAACCACC    870

CCAACCCAAA CAAAAGTCAT TCCAAAGTG ACGGAACGAC CGCCGCTCCC GTGTTCCCCA     930

AACATGTATT TATGTATAAG TAAGCCATTA AATGAATAAT ATTTTGATAA TAATATGGTT    990

TTCTTTTGTA CGAAAGCACA GATCTACTTT GTGGACCAAT CCTTGAGTTA TATATGAGAT   1050

AGAATATATA TATATAATAC TGCTACTAA                                    1079
```

(2) INFORMATION FOR SEQ ID NO:7:

(i) SEQUENCE CHARACTERISTICS:
    (A) LENGTH: 172 aa
    (B) TYPE: amino acid
    (C) STRANDEDNESS: single
    (D) TOPOLOGY: linear (xi) SEQUENCE DESCRIPTION: SEQ ID NO:7:

```
Met Ser Gly Asn Val Tyr Lys Thr Leu Leu Thr Leu Leu Val Tyr Gly
1               5                   10                  15

Leu Ile Met His Cys Asn Val Tyr Cys Ser Pro Asp Arg Trp Thr Pro
            20                  25                  30

Val Pro Gly Ala Lys Leu Glu Glu Val Tyr Asp Glu Asp Gly Asn
        35                  40                  45

Thr Leu Gln Asp Phe Ala Leu Arg Ala Gly Pro Gly Gly Gly
    50                  55                  60

Pro Arg Pro Arg Trp Gly Arg Cys Thr Ala Leu Tyr Tyr Pro Pro Gly
65                  70                  75                  80

Lys Arg His Ala Asp Gly Ile Phe Ser Lys Ala Tyr Arg Lys Leu Leu
                85                  90                  95

Gly Gln Leu Ser Ala Arg Asn Tyr Leu His Ser Leu Met Ala Lys Arg
            100                 105                 110

Val Gly Ser Gly Leu Gly Asp Glu Ala Glu Pro Leu Ser Lys Arg His
        115                 120                 125

Ile Asp Gly Ile Phe Thr Asp Ser Tyr Ser Arg Tyr Arg Lys Gln Met
    130                 135                 140

Ala Val Lys Lys Tyr Leu Ala Ala Val Leu Gly Lys Arg Tyr Lys Gln
145                 150                 155                 160

Arg Val Lys Asn Lys Gly Arg Arg Val Ala Tyr Leu
                165                 170
```

(2) INFORMATION FOR SEQ ID NO:8:

(i) SEQUENCE CHARACTERISTICS:
        (A) LENGTH: 43 aa
        (B) TYPE: amino acid
        (C) STRANDEDNESS: single
        (D) TOPOLOGY: linear (xi) SEQUENCE DESCRIPTION: SEQ ID NO:8:

```
His Ala Asp Gly Ile Phe Ser Lys Ala Tyr Arg Lys Leu Leu Gly Gln
1               5                   10                  15

Leu Ser Ala Arg Asn Tyr Leu His Ser Leu Met Ala Lys Arg Val Gly
            20                  25                  30

Ser Gly Leu Gly Asp Glu Ala Glu Pro Leu Ser
        35                  40
```

(2) INFORMATION FOR SEQ ID NO:9:

(i) SEQUENCE CHARACTERISTICS:
        (A) LENGTH: 992 bp
        (B) TYPE: nucleic acid
        (C) STRANDEDNESS: single
        (D) TOPOLOGY: linear (xi) SEQUENCE DESCRIPTION: SEQ ID NO:9:

| | |
|---|---|
| GCGAATATTG ACAGCCCCCC TTTTTTTTCC TTTATTTGTC GAGTCGATTC | 50 |
| CCTAACCACC CAACAACTCT CTGCGCTTCT GCGCCTTCTT CATCCTTGCC | 100 |
| CAGCGGAAAA GCCGGGAGCC CTTTGACTCT TTCGGCCGCA ACTTGGGGAG | 150 |
| ATAGCTCTAT TTTTCCCCCC TCCTCTCTGG GGTTTTTCTC CTTTTTCCTC | 200 |

```
TCTCCCTTTC CCTTCCGCAG CCACACGCTC TCAGTGCCGG GTGTCACAGT                250

TTC ATG AGT GGC AAT GTG TAT AAA ACG CTC TTA ACC CTC CTG                292
    Met Ser Gly Asn Val Tyr Lys Thr Leu Leu Thr Leu Leu
    1               5                   10

GTC TAT GGA TTA ATA ATG CAT TGC AAC GTC TAC TGC TCA CCC                334
Val Tyr Gly Leu Ile Met His Cys Asn Val Tyr Cys Ser Pro
        15                  20                  25

GAC CGT TGG ACT CCA GTA CCC GGC GCT AAG CTG GAG GAG GAG                376
Asp Arg Trp Thr Pro Val Pro Gly Ala Lys Leu Glu Glu Glu
            30                  35                  40

GTA TAC GAC GAG GAC GGG AAT ACC CTA CAG GAC TTC GCA CTA                418
Val Tyr Asp Glu Asp Gly Asn Thr Leu Gln Asp Phe Ala Leu
                45                  50                  55

CGA GCA GGA GCC CCT GGG GGT GGC GGG CCG CGC CCG CGC TGG                460
Arg Ala Gly Ala Pro Gly Gly Gly Gly Pro Arg Pro Arg Trp
                    60                  65

GGC AGG TGT ACG GCG CTG TAC TAC CCG CCG GGA AAG AGC GGT                502
Gly Arg Cys Thr Ala Leu Tyr Tyr Pro Pro Gly Lys Ser Gly
70                  75                  80

GCC AGC AGC GGC CTG GGG GAC GAG GCG GAA CCG CTC AGC AAG                544
Ala Ser Ser Gly Leu Gly Asp Glu Ala Glu Pro Leu Ser Lys
        85                  90                  95

CGC CAC ATA GAC GGC ATC TTC ACG GAC AGC TAC AGC CGC TAC                586
Arg His Ile Asp Gly Ile Phe Thr Asp Ser Tyr Ser Arg Tyr
            100                 105                 110

GGG AAA CAA ATG GCT GTC AAG AAA TAC TTA GCG GCC GTC CTG                628
Arg Lys Gln Met Ala Val Lys Lys Tyr Leu Ala Ala Val Leu
                115                 120                 125

GGG AAA AGG TAT AAA CAA AGA GTT AAA AAC AAA GGA CGC CGA                670
Gly Lys Arg Tyr Lys Gln Arg Val Lys Asn Lys Gly Arg Arg
                    130                 135

GTA GCG TAT TTG TAG GATGA GCAACCGCCG CTGCCGTGCG TAGTCCTGAG             720
Val Ala Tyr Leu
140

AGAGAGAGAG AGAGAGAGAG AGAGATTGAG AGAGAGAGAG AGAGAGAGAG                 770

AGACCCAACC ACCCCAACCC AAACAAAAGT CATTTCCAAA GTGACGGAAC                 820

GACCGCCGCT CCCGTGTTCC CCAAACATGT ATTTATGTAT AAGTAAGCCA                 870

TTAAATGAAT AATATTTTGA TAATAATATG GTTTTCTTTT GTACGAAAGC                 920

ACAGATCTAC TTTGTGGACC AATCCTTGAG TTATATATGA GATAGAATAT                 970

ATATATATAA TACTGCTACT AA                                               992
```

(2) INFORMATION FOR SEQ ID NO:10:

(i) SEQUENCE CHARACTERISTICS:
    (A) LENGTH: 143 aa
    (B) TYPE: amino acid
    (C) STRANDEDNESS: single
    (D) TOPOLOGY: linear (xi) SEQUENCE DESCRIPTION: SEQ ID NO:10:

```
Met Ser Gly Asn Val Tyr Lys Thr Leu Leu Thr Leu Leu Val Tyr Gly
1               5                   10                  15

Leu Ile Met His Cys Asn Val Tyr Cys Ser Pro Asp Arg Trp Thr Pro
            20                  25                  30

Val Pro Gly Ala Lys Leu Glu Glu Glu Val Tyr Asp Glu Asp Gly Asn
        35                  40                  45
```

```
Thr Leu Gln Asp Phe Ala Leu Arg Ala Gly Ala Pro Gly Gly Gly Gly
    50                  55                  60

Pro Arg Pro Arg Trp Gly Arg Cys Thr Ala Leu Tyr Tyr Pro Pro Gly
65                  70                  75                  80

Lys Ser Gly Ala Ser Ser Gly Leu Gly Asp Glu Ala Glu Pro Leu Ser
                85                  90                  95

Lys Arg His Ile Asp Gly Ile Phe Thr Asp Ser Tyr Ser Arg Tyr Arg
                100                 105                 110

Lys Gln Met Ala Val Lys Lys Tyr Leu Ala Ala Val Leu Gly Lys Arg
                115                 120                 125

Tyr Lys Gln Arg Val Lys Asn Lys Gly Arg Arg Val Ala Tyr Leu
                130                 135                 140

(2) INFORMATION FOR SEQ ID NO:11:

(i) SEQUENCE CHARACTERISTICS:
        (A) LENGTH: 129bp
        (B) TYPE: nucleic acid
        (C) STRANDEDNESS: single
        (D) TOPOLOGY: linear (xi) SEQUENCE DESCRIPTION: SEQ ID NO:11:

CAC GCC GAT GGG ATC TTC AGC AAA GCC TAC AGG AAA CTC CTG GGC CAG       48
His Ala Asp Gly Ile Phe Ser Lys Ala Tyr Arg Lys Leu Leu Gly Gln
                5                   10                  15

CTG TCC GCA AGA AAT TAC CTG CAC TCC CTG ATG GCC AAG CGG GTC GGC       96
Leu Ser Ala Arg Asn Tyr Leu His Ser Leu Met Ala Lys Arg Val Gly
                20                  25                  30

AGC GGC CTG GGG GAC GAG GCG GAA CCG CTC AGC                          129
Ser Gly Leu Gly Asp Glu Ala Glu Pro Leu Ser
                35                  40

(2) INFORMATION FOR SEQ ID NO:12:

(i) SEQUENCE CHARACTERISTICS:
        (A) LENGTH: 138bp
        (B) TYPE: nucleic acid
        (C) STRANDEDNESS: single
        (D) TOPOLOGY: linear (xi) SEQUENCE DESCRIPTION: SEQ ID NO:12:

CAC GCC GAT GGG ATC TTC AGC AAA GCC TAC AGG AAA CTC CTG GGC CAG       48
His Ala Asp Gly Ile Phe Ser Lys Ala Tyr Arg Lys Leu Leu Gly Gln
1               5                   10                  15

CTG TCC GCA AGA AAT TAC CTG CAC TCC CTG ATG GCC AAG CGG GTC GGC       96
Leu Ser Ala Arg Asn Tyr Leu His Ser Leu Met Ala Lys Arg Val Gly
                20                  25                  30

GGT GCC AGC AGC GGC CTG GGG GAC GAG GCG GAA CCG CTC AGC              138
Gly Ala Ser Ser Gly Leu Gly Asp Glu Ala Glu Pro Leu Ser
                35                  40                  45

(2) INFORMATION FOR SEQ ID NO:13:

(i) SEQUENCE CHARACTERISTICS:
        (A) LENGTH: 114bp
        (B) TYPE: nucleic acid
        (C) STRANDEDNESS: single
        (D) TOPOLOGY: linear (xi) SEQUENCE DESCRIPTION: SEQ ID NO:13:

CAC ATA GAC GGA ATC TTC ACG GAC AGC TAC AGC CGC TAC CGG AAA CAA       48
His Ile Asp Gly Ile Phe Thr Asp Ser Tyr Ser Arg Tyr Arg Lys Gln
1               5                   10                  15
```

```
ATG GCT GTC AAG AAA TAC TTA GCG GCC GTC CTG GGG AAA AGG TAT AAA      96
Met Ala Val Lys Lys Tyr Leu Ala Ala Val Leu Gly Lys Arg Tyr Lys
        20                  25                  30

CAA AGA GTT AAA AAC AAA                                              114
Gln Arg Val Lys Asn Lys
        35
```

(2) INFORMATION FOR SEQ ID NO:14:

(i) SEQUENCE CHARACTERISTICS:
        (A) LENGTH: 27bp
        (B) TYPE: nucleic acid
        (C) STRANDEDNESS: single
        (D) TOPOLOGY: linear (xi) SEQUENCE DESCRIPTION: SEQ ID NO:14:

CATGTTTGGA CAGAACACAA GTGAGCG                                        27

(2) INFORMATION FOR SEQ ID NO:15:

(i) SEQUENCE CHARACTERISTICS:
        (A) LENGTH: 26bp
        (B) TYPE: nucleic acid
        (C) STRANDEDNESS: single
        (D) TOPOLOGY: linear (xi) SEQUENCE DESCRIPTION: SEQ ID NO:15:

CATTCGGATG GGATCTTCAC GGATAG                                         26

(2) INFORMATION FOR SEQ ID NO:16:

(i) SEQUENCE CHARACTERISTICS:
        (A) LENGTH: 24bp
        (B) TYPE: nucleic acid
        (C) STRANDEDNESS: single
        (D) TOPOLOGY: linear (xi) SEQUENCE DESCRIPTION: SEQ ID NO:16:

GAGCCCCGCC CGTGCTTACC GCAG                                           24

(2) INFORMATION FOR SEQ ID NO:17:

(i) SEQUENCE CHARACTERISTICS:
        (A) LENGTH: 24bp
        (B) TYPE: nucleic acid
        (C) STRANDEDNESS: single
        (D) TOPOLOGY: linear (xi) SEQUENCE DESCRIPTION: SEQ ID NO:17:

CACGCCGATG GGATCTTCAG CAAA                                           24

(2) INFORMATION FOR SEQ ID NO:18:

(i) SEQUENCE CHARACTERISTICS:
        (A) LENGTH: 24bp
        (B) TYPE: nucleic acid
        (C) STRANDEDNESS: single
        (D) TOPOLOGY: linear (xi) SEQUENCE DESCRIPTION: SEQ ID NO:18:

CCCGACCCGC TTGGCCATCA GGGA                                           24

(2) INFORMATION FOR SEQ ID NO:19:

(i) SEQUENCE CHARACTERISTICS:
        (A) LENGTH: 27 aa
        (B) TYPE: amino acid

```
            (C) STRANDEDNESS: single
            (D) TOPOLOGY: linear (xi) SEQUENCE DESCRIPTION: SEQ ID NO:19:

His Ile Asp Gly Ile Phe Thr Asp Ser Tyr Ser Arg Tyr Arg Lys Gln
1               5                   10                  15

Met Ala Val Lys Lys Tyr Leu Ala Ala Val Leu
            20                  25

(2) INFORMATION FOR SEQ ID NO:20:

(i) SEQUENCE CHARACTERISTICS:
        (A) LENGTH: 29 aa
        (B) TYPE: amino acid
        (C) STRANDEDNESS: single
        (D) TOPOLOGY: linear (xi) SEQUENCE DESCRIPTION:  SEQ ID NO:20:

His Ala Asp Gly Ile Phe Ser Lys Ala Tyr Arg Lys Leu Leu Gly Gln
1               5                   10                  15

Leu Ser Ala Arg Asn Tyr Leu His Ser Leu Met Ala Lys
            20                  25
```

CHICKEN NEUROPEPTIDE GENE USEFUL FOR IMPROVED POULTRY PRODUCTION

FIELD OF THE INVENTION

This invention relates to the improvement of poultry production through the use of recombinant neuropeptides. The invention is premised on the discovery of gene sequences from chicken encoding the neuropeptides GRF (Growth Hormone Releasing Hormone) and PACAP (Pituitary Adenylate Cyclase-Activating Polypeptide).

BACKGROUND OF THE INVENTION

Poultry is a major source of protein in the western diet. However, the result of many years of breeding selection for fast-growing chickens and turkeys has resulted in the production of commercial poultry strains which have increased fat deposits. Because of this increased fat content, some nutritionists no longer recommend poultry over trimmed red meat. In addition, four times as much feed is required to produce 1 gram of fat compared to 1 gram of muscle, and so this increased fat content also elevates production costs (notably, the cost of feed represents over half of the expense of raising poultry—696 for broiler chickens, 61% for turkeys). Accordingly, the ability to produce poultry with a lower fat content would have both health and economic benefits.

Growth Hormone-Releasing Hormone (GHRH or GRF) and Pituitary Adenylate Cyclase-Activating Polypeptide (PACAP) are two members of the glucagon superfamily of proteins. They are neuropeptides which, amongst other activities, stimulate the release of pituitary growth hormone (GH), the major growth hormone in animals. In human studies, recombinant GH has been shown to increase lean body mass and reduce fat content in elderly adults. By extrapolation, the regulation of GH in agricultural animals may be useful to control growth rates and body composition. Accordingly, there is much interest in GRF and PACAP, and a major focus of the ongoing research is the search for genes which encode these neuropeptides in agriculturally important animal species, including poultry.

Although rat and human GRF have been shown to stimulate GH release from chicken pituitary cells in vitro, a chicken GRF has not yet been reported. It is a goal of the present invention to provide neuropeptide gene sequences and peptide sequences which function to stimulate GH release in poultry.

SUMMARY OF THE INVENTION

This invention provides, for the first time, a gene from chicken which encodes a precursor polypeptide for both GRF and PACAP (this gene is referred herein to as the chicken GRF/PACAP gene). The chicken GRF/PACAP gene sequence is provided, along with 5' and 3' regulatory sequences which regulate expression of the gene. Also provided are the amino acid sequences of the peptides encoded by this gene (because of alternative splicing of the introns in the gene, three different mRNAs, encoding three slightly different peptides, are produced). This invention permits the generation of nucleotide sequences encoding either the GRF/PACAP precursor polypeptide or the individual GRF or PACAP peptides, or both of these individual peptides.

Other aspects of the invention involve recombinant cloning vectors including nucleotide sequences encoding the chicken GRF and/or PACAP peptides, and transgenic host cells transformed with such cloning vectors. Genetic constructs designed for optimal expression of the chicken PACAP and/or GRF peptides are also provided. These constructs include nucleotides encoding the chicken GRF/PACAP precursor peptide or the individual chicken PACAP or GRF peptides in association with regulatory sequences which control the expression of the coding sequences. For example, a cDNA molecule encoding the chicken GRF may be functionally linked to the 5' promoter region found upstream of the chicken GRF/PACAP gene.

Also encompassed by this invention are nucleotide sequences which include less than the entire chicken GRF/PACAP gene. For example, oligonucleotide primer and probe sequences which are derived from the nucleotide sequences provided are included within the scope of the invention Such sequences, which are typically 10–50 nucleotides in length are useful, amongst other things, for amplifying the chicken gene from various tissues, performing hybridization studies and for cloning corresponding gene sequences from other species. Nucleotide sequences which encode larger sub-parts of the chicken GRF/PACAP are also part of the invention. Such sequences include, for example, DNA molecules encoding the individual GRF and PACAP peptides, as well as regulatory regions useful in controlling gene expression. These sequences preferably include at least 10 contiguous nucleotides of the disclosed GRF/PACAP gene sequence (and more preferably at least 25, 30 or at least 50 contiguous nucleotides). In other embodiments, these nucleotide sequences encode a peptide capable of stimulating the release of pituitary growth hormone from chicken pituitary cells.

The provision of the chicken GRF/PACAP gene sequence also enables the cloning of related genes from other species, and the production of variants on the disclosed gene sequence. These variant sequences are defined as sequences which hybridize under conditions of at least 75%. stringency to the disclosed sequences and which retain the characteristic of encoding a polypeptide capable of stimulating the release of pituitary growth hormone from chicken pituitary cells.

Another aspect of the invention are the purified chicken GRF and PACAP peptides. The peptides may be purified from cell extracts, for example from host cells transformed with a recombinant vector expressing the peptides, or they may be synthesized by standard peptide synthesis methods. Purified GRF and PACAP peptides may be administered to animals directly to modulate GH levels and thereby regulate body composition and growth rates. For example, the purified peptides may be administered orally to chicks in feed, or may be formulated into slow release pellets which are administered subcutaneously. Such slow-release pellets comprise the peptide combined with a biocompatible matrix, such as cholesterol. Other methods of administration include injection of the peptides incorporated into a biocompatible matrix, and the use of mini osmotic pumps. The amino acid sequences of the disclosd GRF, PACAP and GRF/PACAP precursor polypeptides may also be modified in exact sequence, while retaining the characteristic function of stimulating the release of pituitary growth hormone from chicken pituitary cells. Such variant amino acid sequences preferably include a stretch of at least 20 consecutive amino acids identical to the amino acid sequence of the disclosed peptides.

The nucleotide sequences disclosed herein may also be used to enhance the growth rate or improve the body composition of farmed animals. For example, genetic constructs including the chicken GRF/PACAP gene may be introduced into chicken primordial germ cells to produce genetically altered chickens. Successful integration of such constructs into the chicken genome will produce a bird carrying additional copies of the GRF/PACAP gene which, in turn, would be expected to produce higher levels of the GRF/PACAP polypeptide and thereby elevated levels of pituitary GH. Even higher levels of GRF/PACAP expression may be obtained by using GRF/PACAP constructs in which the open reading frame is operably linked to a promoter known to direct high level expression of downstream gene sequences. Promoter sequences specific for particular tissues (e.g. brain or gonads) or particular developmental stages may also be employed. The present invention also facilitates the ready detection of transgenic birds carrying introduced GRF/PACAP constructs.

BRIEF DESCRIPTION OF THE DRAWINGS

FIG. 2 shows the nucleotide sequence of the chicken GRF/PACAP gene. Nucleotides comprising subclones 1.8, 3.1, and 3.2 are shown along with the intron/exon boundaries and the 5'- and 3'-flanking regions. The translated amino acid sequence is shown in the single letter code below the nucleotide sequence of coded exons and both sequences are numbered on the right. The nucleotide numbering begins at the beginning of the clone, whereas the amino acid numbering begins at the initiating methionine. GRF is underlined with a solid line and PACAP is underlined with a dotted line. All exons are in bold capital letters with the first exon being composed completely of 5' UTR. $GRF_{1-46}$ is encoded on two exons. The intervening inton has alternate splice sites The intron-exon boundary for nucleotides encoding the second part of $GRF_{1-46}$ is shown (+). The other splice site, 9 bp toward the 3' end, is shown by the double symbol (++). This splice site removes nine nucleotides resulting in a shortended $GRF_{1-43}$. Only a portion of the nucleotides that encode the promoter region and intron 2 and 4 are shown. The remaining nucleotides are provided in Seq. I.D. No. 1. Within the promoter, the CAAT and TATAAA sequence motif have been underlined.

SEQUENCE LISTING

Figure 1:
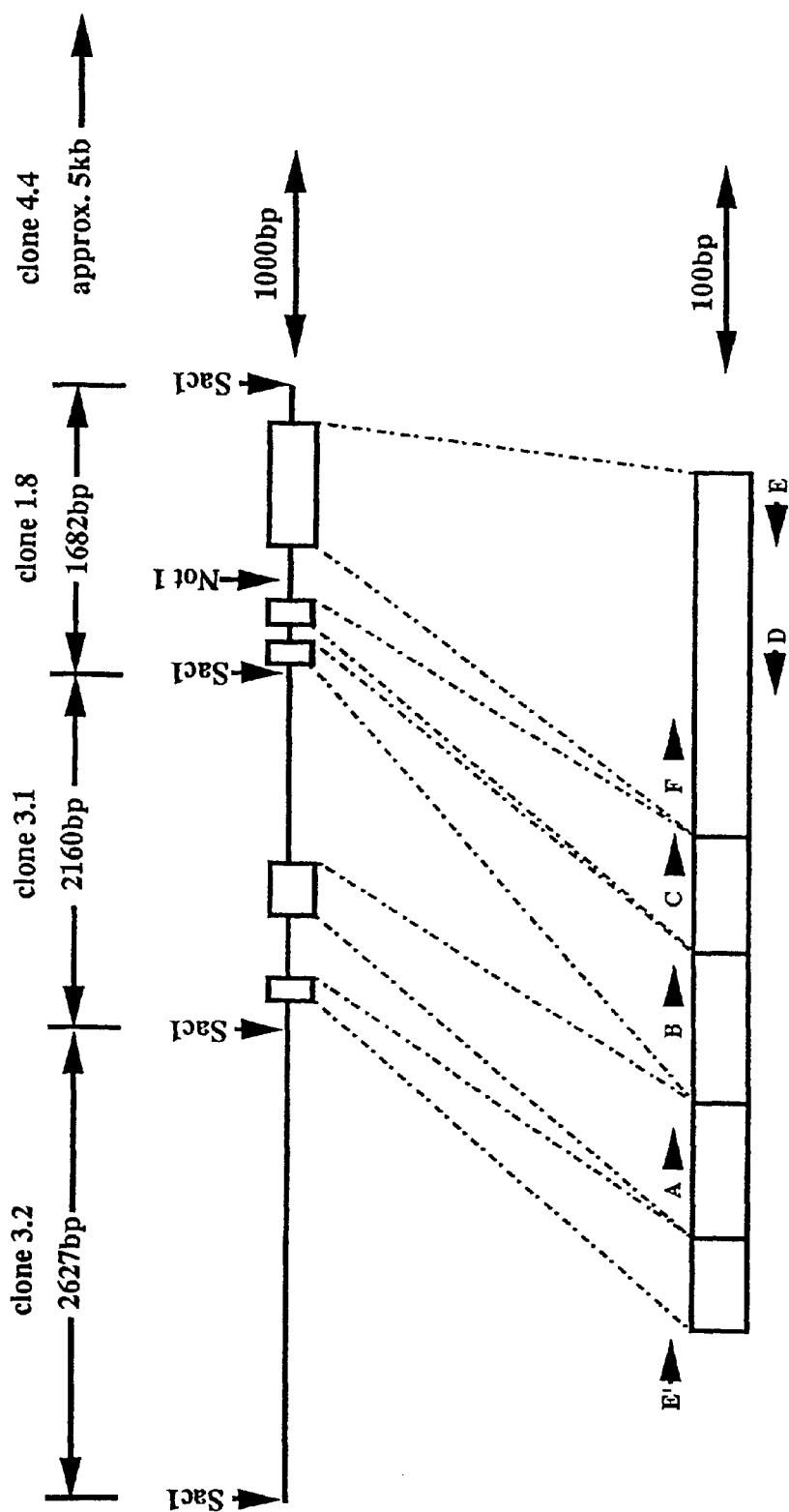
FIG. 1 shows the subclone organization of the chicken GRF/PACAP gene and the cDNA encoding the GRF/PACAP precursor polypeptide, together with the location of PCR primers.

The accompanying sequence listing comprises the following sequence information:

Seq. I.D. No. 1: complete nucleotide sequence of the chicken GRF/PACAP gene.

Seq. I.D. No. 2: full length cDNA encoding chicken GRF/PACAP neuropeptide precursor.

Seq. I.D. No. 3: amino acid sequence of the peptide encoded by full length cDNA shown in Seq. I.D. No. 2 (including 46 amino acid GRF peptide and 38 amino acid PACAP peptide).

Seq. I.D. No. 4: amino acid sequence of the 46 amino acid GRF peptide encoded by full length cDNA shown in Seq. I.D. No. 2.

Seq. I.D. No. 5: amino acid sequence of the 38 amino acid PACAP peptide.

Seq. I.D. No. 6: alternatively spliced cDNA sequence encoding chicken GRF/PACAP neuropeptide precursor (alternatively spliced cDNA #1).

Seq. I.D. No. 7: amino acid sequence of the peptide encoded by alternatively spliced cDNA #1 (including 43 amino acid GRF peptide and 38 amino acid PACAP peptide).

Seq. I.D. No. 8: amino acid sequence of the 43 amino acid GRF peptide encoded by alternatively spliced cDNA #1.

Seq. I.D. No. 9: alternatively spliced cDNA sequence encoding chicken GRF/PACAP neuropeptide precursor (alternatively spliced cDNA #2).

Seq. I.D. No. 10. amino acid sequence of the peptide encoded by alternatively spliced cDNA #2 (including 14 amino acid truncated GRF peptide and 38 amino acid PACAP peptide).

Seq. I.D. No. 11: nucleotide sequence encoding chicken 43 amino acid GRF peptide.

Seq. I.D. No. 12: nucleotide sequence encoding chicken 46 amino acid GRF peptide.

Seq. I.D. No. 13: nucleotide sequence encoding chicken 38 amino acid PACAP peptide.

Seq. I.D. No. 14: nucleotide sequence of primer D used in PCR amplification.

Seq. I.D. No. 15: nucleotide sequence of primer F used in PCR amplification.

Seq. I.D. No. 16: nucleotide sequence of primer A used in PCR amplification.

Seq. I.D. No. 17: nucleotide sequence of primer 1 used in PCR amplification.

Seq. I.D. No. 18: nucleotide sequence of primer 2 used in PCR amplification.

Seq. I.D. No. 19: amino acid sequence of PACAP 27 (PACAP 27 is a form of PACAP which results from alternative post-translational processing).

Seq. I.D. No. 20. amino acid sequence of GRF 29 (the first 29 amino acids of GR, this is believed to represent the minimally active unit of GRF).

DETAILED DESCRIPTION OF THE INVENTION

I. Definitions

Particular terms and phrases used have the meanings set forth below.

Isolated: An "isolated" nucleic acid has been substantially separated or purified away from other nucleic acid sequences in the cell of the organism in which the nucleic acid naturally occurs, i.e., other chromosomal and extrachromosomal DNA and RNA. The term "isolated" thus encompasses nucleic acids purified by standard nucleic acid purification methods. The term also embraces nucleic acids prepared by recombinant expression in a host cell as well as chemically synthesized nucleic acids.

cDNA (complementary DNA): a piece of DNA lacking internal, non-coding segments (introns) and regulatory sequences which determine transcription. cDNA is synthesized in the laboratory by reverse transcription from messenger RNA extracted from cells.

ORF (open reading frame): a series of nucleotide triplets (codons) coding for amino acids without any termination codons. These sequences are usually translatable into a peptide.

Probes and primers: Nucleic acid probes and primers may readily be prepared based on the nucleic acids provided by this invention. A probe comprises an isolated nucleic acid attached to a detectable label or reporter molecule. Typical labels include radioactive isotopes, ligands, chemiluminescent agents, and enzymes. Methods for labeling and guidance in the choice of labels appropriate for various purposes are discussed, e.g., in Sambrook et al. (1989) and Ausubel et al. (1987).

Primers are short nucleic acids, preferably DNA oligonucleotides 15 nucleotides or more in length. Primers may be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, e.g., by the polymerase chain reaction (PCR) or other nucleic-acid amplification methods known in the art.

Methods for preparing and using probes and primers are described, for example, in Sambrook et al. (1989), Ausubel et al. (1987), and Innis et al., (1990). PCR primer pairs can be derived from a known sequence, for example, by using computer programs intended for that purpose such as Primer (Version 0.5, © 1991, Whitehead Institute for Biomedical Research, Cambridge, Mass.).

Purified: the term purified does not require absolute purity; rather, it is intended as a relative term. Thus, for example, a purified peptide or protein preparation is one in which the protein referred to is more pure than the protein in its natural environment within a cell.

Operably linked: A first nucleic acid sequence is operably linked with a second nucleic acid sequence hen the first nucleic acid sequence is placed in a functional relationship with the nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques.

GRF: Growth hormone-releasing hormone (alternatively referred to as GHRH).

PACAP: Pituitary adenylate cyclase-activating polypeptide.

GRF/PACAP precursor polypeptide: a polypeptide which includes both GRF and PACAP polypeptide sequences. Cleavage of this precursor polypeptide yields the individual GRF and PACAP polypeptides and a cryptic polypeptide.

Additional definitions of common terms in molecular biology may be found in Lewin, B. "Genes IV" published by Oxford University Press.

II. Cloning of chicken GRF/PACAP gene

A. Materials and methods

1. DNA amplification i. Amplification of the chicken GRF/PACAP mRNA 3' end

Chicken (*Gallus domesticus*) brains were removed, placed immediately in liquid nitrogen and stored at −80° C. Total RNA was extracted with an acidic guanidinium thiocyanate method (Chomczynski and Sacchi, 1987), followed by purification of poly A⁺ rich mRNA on two consecutive oligo $dT_{12-18}$ columns. Single stranded cDNA was synthesized with 10 µg poly A⁺ rich mRNA, 2 mM oligo $dT_{20}$ (primer E), 5 times Superscript buffer, 2 mM dNTP, 10 mM DTT, 5U RNA guard (Pharmacia), and 200 U RT Superscript (BRL) to a final volume of 25 µl. The reaction was heated to 42° C. for 1.25 hr and terminated by increasing the temperature to 95° C. for 10 min.

Amplification was performed in a 50 µl volume with 0.2 µg cDNA, 5U Taq, 1× Taq buffer (Promega), 200 mM dNTP's, 2.5 mM MgCl₂, and 20 pmol of primers D (5'-catgtttggacagaacacaacgtgagcg) (Seq. I.D. No. 14) and F (5'-cattcggatgggatcttcacggatag) (Seq. I.D. No. 15). The reaction was carried out for 35 cycles at 94° C. for 1 min, 45° C. for 1.5 min, 72° C. for 1.5 min and for a 5.3 min extension at 72° C. Amplified bands were cloned into pBluescript KS+ (Stratagene), electroporated into XL-1 competent cells, and prepared for sequencing with an alkaline hydrolysis method (Birnboim 1983). Both strands were sequenced with [α-³⁵S] dATP using the USB Sequenase chain termination method (Sanger et al., 1977) and CircumVent thermal cycle sequencing kit (New England Biolabs). All sequencing gels were 6% polyacrylamide/7M urea wedge gels, dried under vacuum at 80° C. and exposed to Kodak XAR-5 film for 12–24 h.

ii. Amplification of the 5' end

A modified version of Frohman's (1988) RACE protocol was utilized to amplify the 5' end of the chicken GRF/PACAP cDNA. To amplify the 5' end, 1 µg Poly A+ mRNA was mixed with 10 pmol primer D, and 7 µl DEPC treated water to a final volume of 10 µl, heated at 65° for 5 min, and then cooled on ice. Single stranded cDNA was synthesized with the above mRNA/primer mixture, 5 µl Superscript buffer, 1 µM dNTP, 10 mM DTT, 5U RNA guard (Pharmacia), and 200 U RT Superscript (BRL) to a final volume of 25 µl. The reaction was heated to 42° C. for 1.25 hr and terminated by increasing the temperature to 95° C. for 6 min. The first strand synthesis was concentrated to 12.5 µl, of which 10 µl was extended with dATP, 1 µl water and 1 µl TdT enzyme (BRL). PCR conditions were identical to the above except for the use of primers D and E (oligo $dT_{20}$).

iii. Amplification of GRF/PACAP mRNA splice variants

Brains were removed from 25-day-old chickens and extracted in TriZol (BRL). Complementary DNA was synthesized from 1 µg of total RNA using 200U avian reverse transcriptase (H⁻RT Superscript, BRL), 10 mM DTT, 0.5 mM each dNTP, 50U RNA guard, 2 µM primer E, and 1× H⁻ RT buffer for a total reaction volume of 20 µl. The reaction proceeded for 90 min at 41° C. followed by 10 min at 90° C. PCR amplifications were done with 0.5 µl of newly transcribed single stranded cDNA from each tissue, 5U Taq DNA polymerase, 1× Taq buffer (Promega), 0.2 mM each dNTP, 0.4 µM of primers A (5'-gagccccgcccgtgcttaccgcag) (Seq. I.D. No. 16) and D (FIG. 1), and 2.5 mM MgCl₂ in a 50 µl reaction for 35 cycles (94°(1')-55°(1.5')-72°(1.75'). PCR reactions were purified through a 1.5% agarose gel. Bands were isolated, cloned into pBluescript KS+ (Stratagene), electroporated into XL-1 competent cells, and prepared for sequencing with an alkaline hydrolysis method (Birnboim 1983). Both strands were sequenced with [α-³⁵S] dATP using the USB Sequenase chain termination method (Sanger et al., 1977) and CircumVent thermal cycle sequencing kit (New England Biolabs).

iv. Reverse transcriptase/PCR assay

Brain, ovary/oviduct, testis, pituitary, heart, liver, kidney, crop, small intestine, large intestine, eye, and the muscle were removed from 25-day-old chickens and extracted in TriZol (BRL). Complementary DNA was synthesized from 1 µg of total RNA using 200U avian reverse transcriptase (H⁻ RT Superscript, BRL), 10 mM DTT, 0.5 mM each dNTP, 50U RNA guard, 2 µM primer E, and 1× H⁻ RT buffer for a total reaction volume of 20 µl. The reaction proceeded for 90 min at 41° C. followed by 10 min at 90° C. PCR amplifications were done with 0.5 µl of newly transcribed single stranded cDNA from each tissue, 5U Taq DNA polymerase, 1× Taq buffer (Promega), 0.2 mM each dNTP, 0.4 µM of primers A and D (FIG. 1), and 2.5 mM MgCl₂ in a 50 µl reaction for 35 cycles (94°(1')-55°(1.5)-72°(1.75').

2. Genomic library screening

A total of $10^6$ pfu from the chicken genomic library (Stratagene) were screened with the 294 bp PCR cDNA fragment (primers D/F) Duplicate nylon membrane (BioRad) lifts were prehybridized at 50° C. in 6× SSC, 5× Denhardt's solution, 0.5% SDS and 30 mg/ml sea urchin DNA (blocking DNA) for 4 hours. The hybridization solution, consisting of 6× SSC, 0.5% SDS, and 100 mg blocking DNA, was added to the [$\alpha$-$^{32}$P] dCTP (Dupont) labeled probe ($2.4 \times 10^7$ cpm/ml) and incubated at 50° C. overnight. The membranes were washed under high stringency (0.1× SSC/0.1% SDS) for 50 min at 50° C., then exposed to Kodak XAR-5 film for 7 days at −80° C.

Three additional rounds of screening were used to purify a positive clone that had been isolated from the genomic library. The insert was excised from the phage DNA with Sac1, purified by agarose gel electrophoresis and subcloned into pBluescript KS (Stratagene) using T4 Ligase (Pharmacia). Three of the four Sac1 subclones were shortened by nested deletions (double stranded nested deletion kit, Pharmacia) on both strands followed by sequencing of the two strands, according to the manufacturer's instruction.

3. Southern analysis

Chicken liver DNA was ground and treated with proteinase K (Sigma) in buffer (10 mM Tris, pH 8; 100 mM EDTA, pH 8; 0.5% SDS; 200 $\mu$g/ml proteinase K) overnight at 55° C. The DNA was purified with three subsequent phenol:chloroform:isoamyl alcohol extractions (24:24:1) and one chloroform:isoamyl (24:1) extraction; end-over end mixing was carried out for 3 hours after each addition of fresh phenol-chloroform-isoamyl alcohol. The DNA was dialyzed against TE (pH 8) overnight to remove the organic solvents. 10 $\mu$g (30 $\mu$l) DNA was digested with either EcoRI, Sac1, HindIII, PvuII, and KpnI and electrophoresed through a 1% agarose gel, in duplicate. The DNA was transferred as to the manufacturer's specification (BioRad) for the alkaline Zeta-Probe GT membrane. Prehybridization was in 7% SDS, 0.25M NaHPO$_4$, pH 7.2, 1 mM EDTA at 65° C. for 15 min. Hybridization was in fresh prehybridization solution plus the random primed $\alpha$-$^{32}$P [dCTP] labeled probe for 17 hr at 65° C. The hybridized membranes were rinsed under low stringency (45° C.) with 5% SDS, 40 mM NaHPO$_4$, 1 mM EDTA and then washed for 45 min with fresh solution (45° C.). The wash solution was raised to high stringency (65° C.) by washing with 1% SDS, 40 mM NaHPO$_4$, 1 mM EDTA and washed twice for 45 min at 65° C. with fresh solution. After washing, the membranes were sealed in plastic and exposed 24 hr to Kodak Biomax film with intensifying screens at −80° C.

B. Results

1. Gene organization

A single band of 294 bp resulted from the first DNA amplification of chicken RNA/cDNA. This cDNA fragment was used to screen the chicken genomic library. One million clones were screened to produce a single plaque that hybridized to the probe. The lambda clone of approximately 12500 bp, produced 4 fragments when digested with Sac1 (FIG. 1). These smaller fragments were purified and subcloned into pBluescript KS (subclones 1.8, 3.1, 3.2, and 4.4).

Subclones 1.8, 3.1 and 3.2 contained 6469 bp of the chicken GRF/PACAP gene; clone 4.4 consisted of approximately 5 Kb of 3' flanking region and therefore was omitted. Subclone 1.8 (1682 bp) contained exons 3, 4, and 5 encoding the cryptic peptide, GRF, and PACAP, respectively. Exon 3 containing part of the cryptic peptide was 134 bp in length and contained the nucleotide reading frame that encodes a dibasic processing site (Lys-Arg) between the cryptic and GRF peptide. Exon 4 has 96 nucleotides that code for the initial 32 amino acids of chicken GRF. The final portion of GRF on exon 5 shows that chicken GRF is unique because it is 46 amino acids, the longest known GRF. On exon 5 immediately downstream of the coding region of chicken GRF$_{1-46}$ is the coding region for PACAP$_{1-38}$ separated from GRF by a Lys-Arg processing site. The chicken PACAP$_{1-38}$ is identical to the mammalian form except at position #2 which has an isoleucine substituted for an alanine. Clone 3.1 (2160 bp) contained exon 1 that encoded the 5'-untranslated region (UTR) (194 bp), an intron (142 bp) and exon 2 that encoded the signal peptide and a portion of the cryptic peptide (114 bp). Clone 3.1 also contained 344 bp of regulatory region. Within the 344 bp was a CAAT regulatory region at position 2974 bp, and the TATAA at position 3002 bp; these nucleotides are consensus regulatory regions not found in other pacap genes. Intron 2 of 1337 bp was the longest intron and introns 3 of 178 bp and 4 of 371 bp contained an unusually high G/C content and numerous (G) n repeats. Clone 3.2 (2627 bp) was exclusively promoter.

2. Alternative Splicing

To confirm intron-exon boundaries, brain mRNA/cDNA was screened using the PCR and primers A and D. All intron-exon boundaries were confirmed, however the boundary between exons 4 and 5 was found to vary: in some bands, the first boundary was at position 5703 bp, the second boundary had slid nine bases downstream to position 5712 bp and the third boundary shows that exon 4 is lacking altogether.

3. Tissue expression

In juveniles at 25 days after hatching, chicken GRF/PACAP mRNA was detected not only in the brain, but also in tissues external to the brain using a RT/PCR method. GRF/PACAP mRNA expression was detected within the brain, ovary/oviduct and testis of the chicken. Expression was not detected within the pituitary, heart, liver, kidney, crop, small intestine, large intestine, eye, or the muscle. From the brain mRNA, two bands were amplified from the RT/PCR method. These two bands, along with the single bands from the ovary/oviduct and testis, were purified and sequenced to verify the PACAP sequence. The longest band in the brain and single band in gonads contained all exons, whereas the shorter band in the brain lacked exon 4. The cDNA appeared to be of good quality as determined by the PCR products obtained with tubulin primers.

4. Southern analysis

Southern analysis of chicken genomic DNA using the 294 bp PCR cDNA fragment as a DNA probe revealed two bands. All five genomic DNA restriction digests had two areas hybridizing to the cDNA probe. Both bands appeared when low and high stringency washes were applied to the membrane and no other bands appeared with low stringency washes.

C. Discussion of results

1. Gene organization reveals two neuropeptides encoded in one gene

We have isolated from a chicken (c) genomic library a clone that encodes both a GRF peptide and PACAP. This is the first report of an avian GRF. Both PACAP and GRF belong to the glucagon superfamily in which the members have similar intron/exon organization and sequence identity. For example, the amino acid identity between chicken GRF and PACAP is 30%. This organization in which both peptides are encoded on the same gene is similar to that in fish (see U.S. patent application Ser. No. 08/062,472, now U.S. Pat. No. 5,695,954) but unlike mammals, which have two genes encoding each peptide separately.

The association of chicken PACAP (cPACAP) with members of a superfamily including glucagon, secretin, GRF, and vasoactive intestinal peptide (VIP) is illustrated by a high sequence identity between cPACAP and cVIP (Talbot et al., 1995). In comparing mRNAs, the nucleotides encoding the cPACAP region have 80% identity with the nucleotides encoding the cVIP region. This high degree of identity likely explains the observation of two bands hybridizing with the cPACAP probe on Southern blots.

The nucleotides of the cPACAP coding region are 92% identical to the human PACAP gene. The deduced cPACAP amino acid sequence is 97% identical to the human sequence with the only change being at position 2 where an isoleucine is substituted for an alanine. In contrast, the chicken GRF (cGRF) peptide has only 42% amino acid identity to human, 47% to rat and 76% to carp GRF (Vaughan et al., 1992). This divergence among species is not surprising in view of the relatively low sequence identity of 68% between human and rat GRF.

2. Alternative splicing produces 3 different mRNAs

The chicken GRF/PACAP gene is composed of 5 exons. All 5 exon locations and intron/exon boundaries were confirmed by isolating cDNA clones from the 5' and 3' RACE reactions with adult brain cDNA (FIG. 5). However, in sequences of the PCR fragments, we observed that the intron/exon boundary between exons 4 and 5 has considerable variation (FIG. 5). The dominate boundary occurs at position 5703 bp; the second boundary slides 9 bp downstream to position 5712; and the third boundary shows that exon 4 is lacking altogether. At both splice sites nine bases apart, proper consensus splice sites exist. Therefore, the chicken GRF/PACAP mRNA transcript has splice donor sites that encode a 43-amino-acid GRF. The acceptor site was also shown to shift 9 bp upstream to encode a GRF of 46 residues. The intron nucleotides at the 5' splice site of intron 4, AG:GT(A) and the last 4 nucleotides of intron 4 at both 3' splice sites (NCAG:C), closely match the splice site consensus sequences as found in vertebrates (Padgett et al., 1986; Green 1991).

This pattern of alternative splicing has not been reported for transcripts in this family of peptides. The function of the alternative splicing is not known other than to encode two GRFs of different length with, potentially, two different functions. Recent evidence suggests that human $GRF_{1-44}$ in the chicken may affect somatotroph differentiation in the embryonic chicken pituitary (Porter et al., 1995) and the development of chick neuroblasts and their neurotransmitters (Kentori and Vernadakis 1990). These effects on early brain development and GH-releasing somatotrophs in the pituitary may reflect an early role of $GRF_{1-43}$ and/or $GRF_{1-46}$ in avian systems.

The final mRNA transcript synthesized is a cDNA for chicken GRF/PACAP that lacks exon 4, which encodes $GRF_{1-32}$. The critical part of the peptide is thought to be contained in the missing sequence as mammalian $GRF_{1-29}$ is the core required for full biological activity (Ling et al., 1984). The importance of GRF during development is implied by the absence of exon deletion in the embryo prior to hatching. This deletion of exon four has been reported for cDNAs from three other family members (Parker et al., 1993; Seugkwon et al., 1995; Talbot et al., 1995).

As a result of this alternative splicing, three cDNA sequences may be derived from the GRF/PACAP gene. They are as follows:

1. "Full length" cDNA (Seq. I.D. No. 2) encoding GRF/PACAP precursor polypeptide (Seq. I.D. No. 3) including 46 amino acid GRF peptide (Seq. I.D. No. 4) and 38 amino acid PACAP peptide (Seq. I.D. No. 5).

2. "Alternatively spliced cDNA #1" (Seq. I.D. No. 6) encoding GRF/PACAP precursor polypeptide (Seq. I.D. No. 7) including 43 amino acid GRF peptide (Seq. I.D. No. 8) and 38 amino acid PACAP peptide (Seq. I.D. No. 5).

3. "Alternatively spliced cDNA #2" (Seq. I.D. No. 9) encoding GRF/PACAP precursor polypeptide (Seq. I.D. No. 10) including the presumptively non-functional 14 amino acid truncated GRF peptide and 38 amino acid PACAP peptide (Seq. I.D. No. 5).

The nucleotide sequences comprising the open reading frames of the 43 and 46 amino acid GRFs and the 38 amino acid PACAP are shown in Seq. I.D. Nos. 11, 12 and 13, respectively.

III. Physiological activity of GRF/PACAP neuropeptides

In animal systems studied to date, purified GRF and PACAP have been shown to stimulate the release of GH. For example, PACAP releases GH from mouse and rat clonal pituitary cell lines (Propato-Mussafiri et al., 1992), and human GRF initiates the release of GH from chicken pituitary cells both in vitro (Perez et al., 1987) and in vivo (Scanes and Harvey, 1984). The ability of purified GRF and PACAP to stimulate GH release may therefore be regarded as a defining functional characteristic of these peptides.

The ability of the chicken GRF and PACAP peptides to stimulate the release of GH from chicken pituitary cells may readily be confirmed using the procedure described by Perez et al. (1987, incorporated herein by reference). The assay procedure described by Perez et al. (1987) may also be used to determine whether variant forms of the chicken GRF and PACAP peptides, produced as described in Section V below, retain the ability to stimulate GH release.

IV. Preferred method for making GRF/PACAP genes and cDNAs

The foregoing discussion describes the original means by which the chicken GRF/PACAP gene was obtained and also provides the nucleotide sequence of this gene and of cDNAs produced from this gene. With the provision of this sequence information, the polymerase chain reaction (PCR) may now be utilized in a more direct and simple method for producing the GRF/PACAP gene and the disclosed cDNA sequences.

To amplify the cDNA sequences, total RNA is extracted from chicken brain cells as described above. The extracted RNA is then used as a template for performing the reverse transcription-polymerase chain reaction (RT-PCR) amplification of cDNA. Methods and conditions for RT-PCR are described above and in Kawasaki et al. (1990). The selection of PCR primers will be made according to the portions of the cDNA which are to be amplified. Primers may be chosen to amplify small segments of a cDNA or the entire cDNA molecule. Variations in amplification conditions may be required to accommodate primers of differing lengths; such considerations are well known in the art and are discussed in Innis et al. (1990). For example, the open reading frame of the chicken GRF cDNA molecule may be amplified using the following combination of primers:

primer 1 5' CACGCCGATGGGATCTTCAGCAAA 3' (Seq. I.D. No. 17)

primer 2 5' CCCGACCCGCTTGGCCATCAGGGA 3' (Seq. I.D. No 18)

These primers are illustrative only; it will be appreciated by one skilled in the art that many different primers may be derived from the provided cDNA sequence in order to amplify particular regions of the cDNAs encoding GRF, PACAP or the GRF/PACAP precursor.

Alternatively, the gene sequence encoding the GRF/PACAP precursor polypeptide (i.e. the genomic sequence including introns) or pieces thereof may be obtained by amplification using primers based on the presented gene sequence and genomic chicken DNA as a template.

V. Production of GRF/PACAP sequence variants

It will be apparent to one skilled in the art that the biochemical activity of the chicken GRF and PACAP peptides may be retained even though minor variations are made to the nucleotide sequences encoding them. Thus, a nucleic acid sequence could be designed that encodes for the chicken GRF peptide, but which differs by reason of the redundancy of the genetic code, from the exact GRF cDNA sequence disclosed herein. Therefore, the degeneracy of the genetic code further widens the scope of the present invention as it enables major variations in the nucleotide sequence of a DNA molecule while maintaining the amino acid sequence of the encoded protein.

For example, the seventh amino acid residue in the chicken GRF peptide is serine. This is encoded in the GRF gene by the nucleotide codon triplet AGC. Because of the degeneracy of the genetic code, five other nucleotide codon triplets—TCT, TCA, TCG, TCC, and AGT—also code for serine. Accordingly, the nucleotide sequence of the GRF gene or cDNA could be changed at this position to any one of these five codons without affecting the amino acid composition of the encoded GRF peptide or the functional characteristics of the peptide. The genetic code and variations in nucleotide codons for particular amino acids is presented in Tables 1 and 2. Based upon the degeneracy of the genetic code, variant DNA molecules may be derived from the DNA sequences disclosed herein using standard DNA mutagenesis techniques, or by direct chemical synthesis of DNA sequences.

TABLE 1

The Genetic Code

| First Position (5' end) | Second Position | | | | Third Position (3' end) |
|---|---|---|---|---|---|
| | T | C | A | G | |
| T | Phe | Ser | Tyr | Cys | T |
| | Phe | Ser | Tyr | Cys | C |
| | Leu | Ser | Stop (och) | Stop | A |
| | Leu | Ser | Stop (amb) | Trp | G |
| C | Leu | Pro | His | Arg | T |
| | Leu | Pro | His | Arg | C |
| | Leu | Pro | Gln | Arg | A |
| | Leu | Pro | Gln | Arg | G |
| A | Ile | Thr | Asn | Ser | T |
| | Ile | Thr | Asn | Ser | C |
| | Ile | Thr | Lys | Arg | A |
| | Met | Thr | Lys | Arg | G |
| G | Val | Ala | Asp | Gly | T |
| | Val | Ala | Asp | Gly | C |
| | Val | Ala | Glu | Gly | A |
| | Val (Met) | Ala | Glu | Gly | G |

"Stop (och)" stands for the ocre termination triplet, and "Stop (amb)" for the amber. ATG is the most common initiator codon; GTG usually codes for valine, but it can also code for methionine to initiate an mRNA chain.

TABLE 2

The Degeneracy of the Genetic Code

| Number of Synonymous Codons | Amino Acid | Total Number of Codons |
|---|---|---|
| 6 | Leu, Ser, Arg | 18 |
| 4 | Gly, Pro, Ala, Val, Thr | 20 |
| 3 | Ile | 3 |

TABLE 2-continued

The Degeneracy of the Genetic Code

| Number of Synonymous Codons | Amino Acid | Total Number of Codons |
|---|---|---|
| 2 | Phe, Tyr, Cys, His, Gln, Glu, Asn, Asp, Lys | 18 |
| 1 | Met, Trp | 2 |
| Total number of codons for amino acids | | 61 |
| Number of codons for termination | | 3 |
| Total number of codons in genetic code | | 64 |

Additionally, standard mutagenesis techniques may be used to produce peptides which vary in amino acid sequence from the disclosed GRF and PACAP peptides. Such variant peptides include those with variations in amino acid sequence including minor deletions, additions and substitutions.

While the site for introducing an amino acid sequence variation is predetermined, the mutation per se need not be predetermined. For example, in order to optimize the performance of a mutation at a given site, random mutagenesis may be conducted at the target codon or region and the expressed protein variants screened for the optimal combination of desired activity. Techniques for making substitution mutations at predetermined sites in DNA having a known sequence as described above are well known.

In order to maintain the ability of the GRF/PACAP peptides to stimulate GH release, preferred peptide variants will differ by only a small number of amino acids from the GRF and PACAP peptide sequences disclosed herein. Preferably, such variants will be amino acid substitutions of single residues. Substitutional variants are those in which at least one residue in the amino acid sequence has been removed and a different residue inserted in its place. Such substitutions generally are made in accordance with the following Table 3 when it is desired to finely modulate the characteristics of the protein. Table 3 shows amino acids which may be substituted for an original amino acid in a protein and which are regarded as conservative substitutions.

TABLE 3

| Original Residue | Conservative Substitutions |
|---|---|
| Ala | ser |
| Arg | lys |
| Asn | gln, his |
| Asp | glu |
| Cys | ser |
| Gln | asn |
| Glu | asp |
| Gly | pro |
| His | asn; gln |
| Ile | leu; val |
| Leu | ile; val |
| Lys | arg; gln; glu |
| Met | leu; ile |
| Phe | met; leu; tyr |
| Ser | thr |
| Thr | ser |
| Trp | tyr |
| Tyr | trp; phe |
| Val | ile; leu |

Substantial changes in immunological and functional identity are made by selecting substitutions that are less conservative than those in Table 3, i.e., selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions which in general are expected to produce the greatest changes in protein properties will be those in which (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histadyl, is substituted for (or by) an electronegative residue, e.g., glutamyl or aspartyl; or (d) a residue having a bulky side chain, e.g., phenylalanine, is substituted for (or by) one not having a side chain, e.g., glycine.

The present invention thus encompasses not only the precise GRF/PACAP peptides described herein but also peptides which are derived from those disclosed and which retain the ability to stimulate the release of GH from chicken pituitary cells in vitro. Similarly the scope of the invention is not limited to the precise nucleic acid sequences disclosed.

V. Construction of recombinant vectors for expression of GRF/PACAP peptides in heterologous systems With the provision of the nucleotide sequence for the chicken GRF/PACAP gene and nucleotide sequences encoding the individual chicken GRF and PACAP peptides, this invention enables the construction of recombinant cloning vectors for expressing any combination of the GRF/PACAP precursor polypeptide, the GRF peptide or the PACAP peptide (as well as variants on these sequences, as described in the preceding section). For example, the nucleotide sequence depicted in Seq. I.D. No. 2 may be selected for expression of the full length cDNA encoding the $GRF_{1-46}$/$PACAP_{1-38}$ precursor polypeptide, whereas the sequence shown in Seq. I.D. No. 12 may be selected for expression of $GRF_{1-46}$ alone.

The expression of these open reading frames (ORFs) in heterologous cell systems involves the introduction of the ORF into a vector (such as a plasmid), in such a way that the ORF is operably linked to regulatory sequences to direct transcription of the ORF. The recombinant vector is introduced into the selected host cell, which is then grown under conditions which support the expression of the ORF and production of the peptide sequence. Methods for expressing proteins by recombinant means in compatible prokaryotic or eukaryotic host cells are well known in the art and are discussed, for example, in Sambrook et al. (1989) and in Ausubel et al. (1987).

The most commonly used prokaryotic hosts are strains of *Escherichia coli*, although other prokaryotes, such as *Bacillus subtilis* or Pseudomonas may also be used, as is well known in the art. For expression in a bacterial host, the selected ORF is ligated into bacterial expression vectors. Methods for expressing large amounts of protein from a cloned gene introduced into *Escherichia coli* (*E. coli*) may be utilized for the purification of the peptide. Methods and plasmid vectors for producing fusion proteins and intact native proteins in bacteria are described in Sambrook et al. (1989) (ch. 17). Such fusion proteins may be made in large amounts, are easy to purify, and can be used to produce antibodies. Native proteins can be produced in bacteria by placing a strong, regulated promoter and an efficient ribosome binding site upstream of the cloned gene. If low levels of protein are produced, additional steps may be taken to increase protein production; if high levels of protein are produced, purification is relatively easy.

Often, proteins expressed at high levels are found in insoluble inclusion bodies. Methods for extracting proteins from these aggregates are described in ch. 17 of Sambrook et al. (1989). Vector systems suitable for the expression of lacZ fusion genes include the pUR series of vectors (Ruther et al. (1983)), pEX1-3 (Stanley and Luzio (1984)) and pMR100 (Gray et al. (1982)). Vectors suitable for the production of intact native proteins include pKC30 (Shimatake and Rosenberg (1981)), pKK177-3 (Amann and Brosius (1985)) and pET-3 (Studiar and Moffatt (1986)). Fusion proteins may be isolated from protein gels, lyophilized, ground into a powder and used as antigen preparations.

Mammalian or other eukaryotic host cells, such as those of yeast, filamentous fungi, plant, insect, amphibian or avian species, may also be used for protein expression, as is well known in the art. Examples of commonly used mammalian host cell lines are VERO and HeLa cells, Chinese hamster ovary (CHO) cells, and WI38, BHK, and COS cell lines, although it will be appreciated by the skilled practitioner that other prokaryotic and eukaryotic cells and cell lines may be appropriate for a variety of purposes, e.g., to provide higher expression, desirable glycosylation patterns, or other features.

For expression in mammalian cells, the ORF sequence may be ligated to heterologous promoters, such as the SV40 promoter in the pSV2 vector (Mulligan and Berg, 1981), and introduced into cells, such as monkey COS-1 cells (Gluzman, 1981) co achieve transient or long-term expression. To achieve this, the ORF or a mini gene (a cDNA with an intron and its own promoter) is introduced into eukaryotic expression vectors by conventional techniques. These vectors are designed to permit the transcription of a cDNA in eukaryotic cells by providing regulatory sequences that initiate and enhance the transcription of the cDNA. Vectors containing the promoter and enhancer regions of the SV40 or long terminal repeat (LTR) of the Rous Sarcoma virus and polyadenylation and splicing signal from SV40 are readily available (Mulligan et al., 1981; Gorman et al., 1982). The level of expression of the cDNA can be manipulated with this type of vector, either by using promoters that have different activities (for example, the baculovirus pAC373 can express cDNAs at high levels in *S. frugiperda* cells (Summers and Smith, 1985)) or by using vectors that contain promoters amenable to modulation, for example, the glucocorticoid-responsive promoter from the mouse mammary tumor virus (Lee et al., 1982).

In addition, some vectors contain selectable markers such as the gpt (Mulligan and Berg, 1981) or neo (Southern and Berg, 1982) bacterial genes. These selectable markers permit selection of transfected cells that exhibit stable, long-term expression of the vectors (and therefore the introduced ORF). The vectors can be maintained in the cells as episomal, freely replicating entities by using regulatory elements of viruses such as papilloma (Sarver et al., 1981) or Epstein-Barr (Sugden et al., 1985). Alternatively, one can also produce cell lines that have integrated the vector into genomic DNA. Both of these types of cell lines produce the gene product on a continuous basis. One can also produce cell lines that have amplified the number of copies of the vector (and therefore of the ORF as well) to create cell lines that can produce high levels of the gene product (Alt et al., 1978).

The transfer of DNA into eukaryotic, in particular human or other mammalian cells, is now a conventional technique. The vectors are introduced into the recipient cells as pure DNA (transfection) by, for example, precipitation with calcium phosphate (Graham and vander Eb, 1973) or strontium phosphate (Brash et al., 1987), electroporation (Neumann et al., 1982), lipofection (Felgner et al., 1987), DEAE dextran (McCuthan et al., 1968), microinjection (Mueller et al., 1978), protoplast fusion (Schafner, 1980), or pellet guns (Klein et al., 1987). Alternatively, the cDNA can be introduced by infection with virus vectors. Systems are developed that use, for example, retroviruses (Bernstein et al., 1985), adenoviruses (Ahmad et al.; 1986), or Herpes virus (Spaete et al., 1982).

This invention encompasses in part, recombinant cloning vectors encoding the GRF/PACAP sequence, or portions thereof. The GRF/PACAP sequence is operatively linked in the vector to an expression control sequence in the recombinant DNA molecule so that the GRF/PACAP polypeptide, or a portion thereof, can be expressed in a host cell. The expression control sequence may be selected from the group consisting of sequences that control the expression of genes of prokaryotic or eukaryotic cells and their viruses and combinations thereof. The expression control sequence may be specifically selected from a wide group of characterized regulatory sequences, including the lac system, the trp system, the tac system, the trc system, major operator and promoter regions of phage lambda, the control region of fd coat protein, the early and late promoters of SV40, promoters derived from polyoma, adenovirus, retrovirus, baculovirus and simian virus, the promoter for 3-phosphoglycerate kinase, the promoters of yeast acid phosphatase, the promoter of the yeast alpha-mating factors and combinations thereof.

Another aspect of the present invention is a host cell containing a recombinant vector which encodes the GRF/PACAP precursor polypeptide or the GRF or PACAP peptides.

VII. Formulation of purified peptides for administration to poultry

The chicken GRF/PACAP precursor polypeptide or the individual GRF or PACAP peptides may be purified from host cells as described above. Alternatively, these peptides may be chemically synthesized using common peptide synthesis techniques. An exemplary peptide synthesis technique is described in U.S. Pat. No. 5,326,860, which is incorporated herein by reference.

Once purified, these peptides may be incorporated into slow-release formulations for administration to chicks. Such formulations include the purified peptide and a biocompatible matrix, such as cholesterol. Slow release formulations may take the form of pellets, which can be administered subcutaneously, or may be preparations suitable for injection. The dosage of peptide administered will vary with the predicted speed of release in the body, but will be in the appropximate range of 1 µg–100 mg for a 2 kg chicken. Thus, for example, a pellet for subcutaneous administration may be prepared by combining 30 mg of powdered cholesterol with 1 mg of the selected peptide and compressing the formulation using a standard pellet maker. The peptides may be pelleted alone or in combination (e.g. pellets may be made using just purified GRF, or with GRF combined with PACAP). Formulation of peptides into slow release preparations may be performed according to standard techniques, or may be performed by a commercial supplier of such materials.

VIII. Production of antibodies to GRF and PACAP

Monoclonal antibodies may be produced which bind the chicken GRF/PACAP precursor polypeptide or the individual GRF or PACAP peptides (referred to as the "target peptide"). Optimally, antibodies raised against any of the peptides would specifically detect the target peptide against which they were raised. That is, such antibodies would recognize and bind that peptide and would not substantially recognize or bind to other proteins found in chicken cells. The determination that an antibody specifically detects a particular peptide is made by any one of a number of standard immunoassay methods; for instance, the Western blotting technique (Sambrook et al., 1989). For example, to determine that a given antibody preparation (such as one produced in a mouse) specifically detects the chicken GRF peptide by Western blotting, total cellular protein is extracted from chicken cells (for example, gonad cells) and electrophoresed on a sodium dodecyl sulfate-polyacrylamide gel. The proteins are then transferred to a membrane (for example, nitrocellulose) by Western blotting, and the antibody preparation is incubated with the membrane. After washing the membrane to remove non-specifically bound antibodies, the presence of specifically bound antibodies is detected by the use of an anti-mouse antibody conjugated to an enzyme such as alkaline phosphatase; application of the substrate 5-bromo-4-chloro-3-indolyl phosphate/nitro blue tetrazolium results in the production of a dense blue compound by immuno-localized alkaline phosphatase. Antibodies which specifically detect the GRF peptide will, by this technique, be shown to bind to the GRF peptide band (which will be localized at a given position on the gel determined by its molecular weight). Non-specific binding of the antibody to other proteins may occur and may be detectable as a weak signal on the Western blot. The non-specific nature of this binding will be recognized by one skilled in the art by the weak signal obtained on the Western blot relative to the strong primary signal arising from the specific antibody-GRF peptide binding.

Substantially pure target peptide suitable for use as an immunogen is isolated from the transfected or transformed cells as described above. Concentration of the target peptide in the final preparation is adjusted, for example, by concentration on an Amicon filter device, to the level of a few milligrams per milliliter. Monoclonal antibody to the target peptide can then be prepared as follows:

Monoclonal antibody to epitopes of the target peptide identified and isolated as described can be prepared from murine hybridomas according to the classical method of Kohler and Milstein (1975) or derivative methods thereof. Briefly, a mouse is repetitively inoculated with a few micrograms of the target peptide over a period of a few weeks. The mouse is then sacrificed, and the antibody-producing cells of the spleen isolated. The spleen cells are fused by means of polyethylene glycol with mouse myeloma cells, and the excess unfused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as ELISA, as originally described by Engvall (1980), and derivative methods thereof. Selected positive clones can be expanded and their monoclonal antibody product harvested for use, Detailed procedures for monoclonal antibody production are described in Harlow and Lane (1988).

Monoclonal antibodies raised against the chicken PACAP, GRF or PACAP/GRF precursor peptides are useful in purifying these peptides and in detecting the presence of these peptides using standard biochemical techniques (such as radioimmunoassay, RIA). For example, the antibodies may be used to quantify levels of PACAP or GRF in poultry to which peptide pellets have been administered.

IX. Introduction of GRF/PACAP gene into poultry

The present invention also facilitates the production of transgenic poultry, expressing elevated levels of GRF and/or PACAP. A vector expressing the desired peptide may be produced as described in Section V above. It may be desirable to produce a construct expressing the GRF/PACAP polypeptide (or the individual GRF or PACAP polypeptides) under the control of the native GRF/PACAP gene promoter, such that the introduced construct expresses the encoded peptide in the same cells and at the same developmental stages as the native peptide is expressed. This may be achieved by operably linking the 5' promoter region of the GRF/PACAP gene (identified as nucleotide numbers 1 to 3074 of Seq. I.D. No. 1) to the selected ORF. While nucleotides 1 to 3074 are known to include regions controlling the expression of the native GRF/PACAP gene, one of skill in the art will also recognize that less than this entire sequence may provide satisfactory regulation of gene expression. Similarly all or part of the nucleotide sequence located 3' of the native GRF/PACAP gene (represented as nucleotide numbers 6201 to 6529 of Seq. I.D. No. 1) may be operably linked to the 3' end of the selected ORF.

Higher or constitutive levels of GRF or PACAP expression may be obtained by using GRF/PACAP constructs in which the open reading frame is operably linked to a promoter known to direct high level or constitutive expression of downstream gene sequences. Promoter sequences specific for particular tissues (e.g. brain or gonads) or particular developmental stages may also be employed.

These recombinant vectors can then be introduced into chickens. Standard methods of producing transgenic fish are not suitable for use in chickens, in part because chicken ova are nearly impossible to obtain as they are fertilized inside the hen and begin to divide rapidly long before they are laid as eggs. Recently, new approaches have been developed, including embryonic stem cell methods (Pain et al., 1996) and primordial germ cell (PGC) isolation (Chang et al., 1992). PGCs are the precursors to ova and sperm; they are formed in the hypoblast, then move through the blood to the genital ridge where they settle and remain in the gonads. PGCs may thus be found in the blood of chicken embryos, and may be separated from the blood cells using a Ficoll gradient. Gene constructs may be introduced into the PGCs using a lipid carrier and the injected PGCs injected into host embryos. The host embryos are then incubated, hatched and allowed to mature to reproductive age. These chickens will have extra copies of the gene only in their eggs and sperm., and may be bred conventionally to produce chicks which have the introduced genetic construct in all of their cells (the presence of the construct can readily be detected using standard PCR techniques). Successful transfer of PGCs from one chicken to another has already been achieved with a hatch rate of 18–30% (Naito et al., 1994).

Accordingly, the present invention includes recombinant DNA molecules that include sequences encoding chicken GRF or PACAP peptides or a GRF/PACAP precursor polypeptide, as well as transgenic non-human animals wherein the genome of these animals includes such a recombinant DNA molecule.

X. Cloning of related genes from other species

This invention provides the nucleotide sequence of the chicken GRF/PACAP gene, as well as regulatory sequences associated with this gene. These nucleotide sequences may now be used to obtain corresponding and related sequences from other species. For example, the chicken GRF/PACAP gene sequence may be used as a hybridization probe to isolate corresponding neuropeptide genes from other avian species, such as turkey. Related avian neuropeptide genes may alternatively be obtained using primers derived from the sequences provided herein, in conjunction with standard gene amplification techniques. Hybridization probes and amplification primers useful in such techniques and derived from the disclosed nucleotide sequences are part of the present invention By way of example, related avian neuropeptide genes may be obtained by creating a library of avian cDNA or genomic DNA in a plasmid, bacteriophage or phagemid vector and screening this library with a hybridization probe using standard colony hybridization techniques. The hybridization probe consists of an oligonucleotide derived from the chicken GRF/PACAP gene sequence labeled with a suitable marker to enable detection of hybridizing clones. Suitable markers include radionuclides, such as P-32 and non-radioactive markers, such as biotin. Methods for constructing suitable libraries, production and labelling of oligonucleotide probes and colony hybridization are standard laboratory procedures and are described in standard laboratory manuals such as Sambrook et al. (1989) and Ausubel et al. (1987).

Having identified a clone that hybridizes with the oligonucleotide, the clone is sequenced using standard methods such as described in Chapter 13 of Sambrook et al. (1989). Determination of the translation initiation point of the DNA sequence enables the open reading frame of the cDNA to be determined.

An alternative approach to cloning genes homologous to the disclosed chicken nucleotide sequences is the use of the polymerase chain reaction (PCR). In particular, the inverse polymerase chain reaction (IPCR) is useful to isolate DNA sequences flanking a known sequence. Methods for amplification of flanking sequences by IPCR are described in Chapter 27 of Innis et al. (1990).

Accordingly, within the scope of this invention are small DNA molecules which are derived from the disclosed chicken nucleotide sequence. Such small DNA molecules include oligonucleotides suitable for use as hybridization probes or polymerase chain reaction (PCR) primers. For use in gene amplification techniques, these oligonucleotides will preferably comprise a contiguous stretch of at least 10–15 nucleotides of the chicken sequences shown in Seq. I.D. No. 1 or the salmon sequence shown in Seq. I.D. Nos. 8 or 9. For use as hybridization probes, these oligonucleotides will preferably comprise a contiguous stretch of at least 20–30 nucleotides of these sequences.

Also encompassed in the present invention are nucleotide sequences which are homologous to the chicken GRF/PACAP precursor polypeptide gene and which hybridize to this sequence, or a fragment thereof, under stringent hybridization conditions. Hybridization conditions resulting in particular degrees of stringency will vary depending upon the nature of the hybridization method of choice and the composition and length of the hybridizing DNA used. Generally, the temperature of hybridization and the ionic strength (especially the Na+concentration) of the hybridization buffer will determine the stringency of hybridization. Calculations regarding hybridization conditions required for attaining particular degrees of stringency are discussed by Sambrook et al. (1989), chapters 9 and 11, herein incorporated by reference. By way of illustration only, a hybridization experiment may be performed by hybridization of a DNA molecule to a target DNA molecule which has been electrophoresed in an agarose gel and transferred to a nitrocellulose membrane by Southern blotting (Southern, 1975), a technique well known in the art and described in (Sambrook et al., 1989). Hybridization with a target probe labeled with [$^{32}$P]-dCTP is generally carried out in a solution of high ionic strength such as 6× SSC at a temperature that is 20–25° C. below the melting temperature, Tm, described below. For such Southern hybridization experiments where the target DNA molecule on the Southern blot contains 10 ng of DNA or more, hybridization is typically carried out for 6–8 hours using 1–2 ng/ml radiolabeled probe (of specific activity equal to $10^9$ CPM/μg or greater) Following hybridization, the nitrocellulose filter is washed to remove background hybridization. The washing conditions should be as stringent as possible to remove background hybridization but to retain a specific hybridization signal. The term $T_m$ represents the temperature above which, under the prevailing ionic conditions, the radiolabeled probe molecule will not hybridize to its target DNA molecule. The $T_m$ of such a hybrid molecule may be estimated from the following equation (Bolton and McCarthy, 1962):

$$T_m = 81.5°\,C. - 16.6(\log_{10}[Na^+]) + 0.41(\%\,G+C) - 0.63(\%\,\text{formamide}) - (600/l)$$

Where l=the length of the hybrid in base pairs. This equation is valid for concentrations of $Na^+$ in the range of 0.01 M to 0.4 M, and it is less accurate for calculations of $T_m$ in solutions of higher $[Na^+]$. The equation is also primarily valid for DNAs whose G+C content is in the range of 30% to 75%, and it applies to hybrids greater than 100 nucleotides in length (the behavior of oligonucleotide probes is described in detail in Ch. 11 of Sambrook et al., 1989).

Thus, by way of example, for a 150 base pair DNA probe derived the open reading frame of the chicken GRF/PACAP precursor polypeptide gene (with a hypothetical % GC=45%), a calculation of hybridization conditions required to give particular stringencies may be made as follows:

For this example, it is assumed that the filter will be washed in 0.3× SSC solution following hybridization, thereby $[Na^+]$=0.045M

% GC=45%

Formamide concentration=0 l=150 base pairs $$T_m = 81.5 - 16(\log_{10}[Na^+]) + (0.41 \times 45) - \frac{(600)}{(150)}$$

and so $T_m$=74.4° C.

The $T_m$ of double-stranded DNA decreases by 1–1.5° C. with every 1% decrease in homology (Bonner et al., 1973). Therefore, for this given example, washing the filter in 0.3× SSC at 59.4–64.4° C. will produce a stringency of hybridization equivalent to 90%; that is, oligonucleotides with more than 10% sequence variation relative to the target sequence will not hybridize (such hybridization conditions may be referred to as "conditions of 90% stringency"). Alternatively, washing the hybridized filter in 0.3× SSC at a temperature of 65.4–68.4° C. will yield a hybridization stringency of 94% (conditions of 94% stringency); that is, oligonucleotides with more than 6% sequence variation relative to the target sequence will not hybridize. The above example is given entirely by way of theoretical illustration. One skilled in the art will appreciate that other hybridization techniques may be utilized and that variations in experimental conditions will necessitate alternative calculations for stringency.

The present inventions encompasses nucleic acid molecules which hybridize to the specifc nucleic acid molecules presented in the accompanying sequence listing under conditions of high stringency. In preferred embodiments of the present invention, stringent conditions are those under which DNA molecules with more than 25% sequence variation (also termed "mismatch") will not hybridize. Such hybridization conditions thus represent conditions of 75% stringency. In a more preferred embodiment, stringent conditions are those under which DNA molecules with more than 10% mismatch will not hybridize (conditions of 90% stringency).

REFERENCES

Ahmad et al. (1986), *J. Virol.* 57:267.
Alt et al. (1978), *J. Biol. Chem.* 253:1357.
Amann and Brosius (1985), *Gene* 40:183.
Arimura, A. (1992), *Reg. Pept.*, 37:287–304.
Ausubel et al. (1987), *Current Protocols in Molecular Biology*, ed. Greene Publishing and Wiley-Interscience: New York (with periodic updates).
Bernstein et al. (1985), *Gen. Enqr'q* 7:235.
Birnboim, M. (1983), *Methods Enzymol.*, 100: 243–255.
Bolton and McCarthy (1962), *Proc. Natl. Acad. Sci. USA* 48:1390.
Bonner et al. (1973), *J. Mol. Biol.* 81:123.
Brash et al. (1987), *Mol. Cell Biol.* 7:2013.
Campbell, R. M. and Scanes, C. G. (1992), *Growth Reg.*, 2:175–191.
Chang et al. (1992), *Cell Biology International Reports* 16:853–857.
Chomczynski, P. and Sacchi, N. (1987), *Anal. Biochem.*, 162:156–159.
Culler, M. D. and Paschall, C. S. (1991), *Endocrinology*, 129:2260–2262.
Denver, R. J. and Licht, P. (1989), *J. Exp. Zool.*, 251:306–315.
Denver, R. J. and Licht, P. (1991), *Comp. Biochem. Physiol.*, 100:603–606.
DiCicco-Bloom, E. M. (1994), Pituitary Adenylate Cyclase Activating Polypeptide, *Program of the 24th Annual Meeting of the Society of Neuroscience*, Miami Beach, Florida, p289. (abstract).
Dirksen et al. (1994); *J. Biol. Chem.*, 269:6431–6436.
Felgner et al. (1987), *Proc. Natl. Acad. Sci USA* 84:7413
Frohman, M. A. (1988), *Proc. Natl. Acad. Sci. (USA)*, 8:8998–9002.
Giusti et al. (1986), *J. Endocrinol. Invest.*, 9:497–501.
Gluzman (1981), *Cell* 23:175–182.
Gorman et al. (1982), *Proc. Natl. Acad. Sci USA* 78:6777–6781.
Graham and vander Eb (1973), *Virology* 52:466.
Gray et al. (1982), *Proc. Natl. Acad. Sci. USA* 79:6598.
Green, M. R. (1991), *Annu. Rev. Cell Biol.*, 7:559–599.
Guo et al. (1991), *Genes and Devel.*, 5:2096–2107.
Hannibal, J. and Fahrenkrug, J. (1995), *Req. Pept.*, 55:111–115.
Harlow and Lane (1988). *Antibodies, A Laboratory Manual*, Cold Spring Harbor Laboratory, New York.
Hart, G. R., Gowing, H. and Burrin, J. M. (1992), *J. Endocrinol.*, 134:33–41.
Harvey, S. (1990), *J. Endocrinol.*, 125:345–358.
Huh, G. S. and Hynes, R. O. (1994), *Genes and Devel.*, 8:1561–1574.
Kawasaki et al. (1990). In *PCR Protocols, A Guide to Methods and Applications*, Innis et al. (eds.), 21–27, Academic Press, Inc., San Diego, Calif.
Kentori, S. and Vernadakis, A. (1990), *Brain Res.*, 512:297–303.

Klein et al. (1987), *Nature* 327:70.
Kohler and Milstein (1975), *Nature* 256:495.
Lee et al. (1982), *Nature* 294:228.
Ling et al. (1984), *Biochem. Biophys. Res. Commun.*, 123:854–861.
Luo, D. and McKeown, B. A. (1989), *Experimentia*, 45:577–580.
Luo et al. (1990), *Gen. Comp. Endocrionol.*, 80:288–298.
Malagon et al. (1991), *Gen. Comp. Endocrinol.*, 84:461–469.
McCuthan et al. (1968), *J. Natl Cancer Inst.* 41:351.
McRory et al. (1995), *Mol. Cell Endocrinol.*, 108:169–177.
Moretti et al. (1990), *Endocrinology*, 127:2117–2126.
Mueller et al. (1978), *Cell* 15:579.
Mulligan and Berg (1981), *Proc. Natl. Acad. Sci. USA* 78:2072–2076.
Mullis et al. (1986), *Cold Spring Harbor Symp. Quant. Biol*, 51:263–273.
Murakami et al. (1995), *Reg. Pept.*, 56:35–40.
Naito et al. (1994), *Molecular Reproduction and Development* 39:153–161.
Neumann et al. (1982), *EMBO J* 1:841.
Padgett et al. (1986), *Ann. Rev. Biochem.*, 55:1119–1150.
Pain et al. (1996), *Development* 122:2339–2348.
Parker et al. (1993), *Eur. J. Biochem.*, 215:439–448.
Patten, B. M. (1964), *In: Foundations of Embryology*, pp225–264. McGraw-Hill, Toronto.
Perez, F. M., Malamed, S. and Scanes, C. G. (1987), *Gen. Comp. Endocrinol.*, 65:408–414.
Pesce et al. (1996), *Development*, 122:215–221.
Peter et al. (1984), *J. Exp. Zool.*, 231:161–163.
Porter et al. (1995), *Endocrinology*, 136:1850–1856.
Propato-Mussafiri et al. (1992), *J. Endocrinol.*, 132:107–113.
Rawlings, S. R. and Hezareh, M. (1996), *Endocrine Rev.*, 17:4–29.
Rivier et al. (1982), *Nature* (London), 300:276–278.
Robberecht et al. (1994), *Peptides*, 15:661–665.
Ruther et al. (1983), *EMBO J.* 2:1791.
Sambrook. J., Fritsch, E. F., and Maniatis, T. (1989), *Molecular Cloning, a Laboratory Manual*, 2nd ed., Cold Spring Harbor: Cold Spring Harbor Laboratory Press.
Sanger, F., Nicklen, S. and Coulson, A. R. (1977), *Proc. Natl. Acad. Sci. (USA)*, 74:5463–5467.
Sarver et al. (1981) *Mol. Cell Biol.* 1:486.
Scanes, C. G. and Harvey, S. (1984), *Gen. Comp. Endcrinol.*, 56:198–203.
Schafner (1980). *Proc. Natl. Acad. Sci. USA* 77:2163–2167.
Seungkwon et al. (1995), *Endocrinology* 136:2602–2610.
Sherwood et al. (1994), In: *Fish Physiology*, N. M. Sherwood and C. Hew (eds), 13:3–66 Academic Press, Orlando.
Shimatake and Rosenberg (1981), *Nature* 292:128.
Shuto et al. (1994), *Program of the 24th Annual Meeting of the Society of Neuroscience*, Miami Beach, Fla., 1994, p870 (abstract).
Southern, E. (1975), *J. Mol. Biol.*, 98:503.
Southern and Berg (1982), *J. Mol. Appl. Genet.* 1:327–341.
Spaete et al. (1982), *Cell* 30:295.
Stanley and Luzio (1984), *EMBO J.* 3:1429.
Studiar and Moffatt (1986), *J. Mol. Biol.* 189:113.
Sugden et al. (1985), *Mol. Cell Biol.* 5:410.
Summers and Smith (1985), in *Genetically Altered Viruses and the Environment*, Fields et al. (Eds.) 22:319–328, Cold Spring Harbor Laboratory Press, Cold Spring Harbor, N.Y.
Tacke, R. and Goridis, C. (1991), *Genes and Devel.*, 5:1416–1429.
Talbot et al. (1995), *J. Mol. Endocrinol.*, 15:81–91.
Vale et al. (1983), *Endocrinology*, 112:1553–1555.
Vaughan et al. (1992), *Neuroendocrinology*, 56:539–549.
Watakabe, A., Tanaka, K. and Shimura, Y. (1993), *Genes and Devel.*, 7:407–418.
Xu, R., Teng, J. and Cooper, T. A. (1993), *Mol. Cell Biol.*, 13:3660–3574.
Zahler et al. (1992), SR Proteins: *Genes and Devel.*, 6:837–847.

What is claimed is:

1. An isolated nucleic acid molecule, comprising the nucleic acid sequence as shown in Seq. I.D. No. 1.

2. A vector, comprising a nucleic acid molecule according to claim 1.

3. An isolated host cell, comprising a vector according to claim 2.

4. A method for producing a polypeptide, the method comprising:
   (a) providing an isolated host cell according to claim 3;
   (b) cultivating the host cell under conditions supporting the production of a polypeptide encoded by the nucleic acid molecule; and
   (c) harvesting the polypeptide.

5. An isolated nucleic acid molecule consisting of a nucleic acid sequence as shown in Seq. I.D. No. 1.

6. A vector comprising a nucleic acid molecule according to claim 5.

7. An isolated host cells comprising a vector according to claim 6.

8. A method of producing a polypeptide, the method comprising:
   (a) providing an isolated host cell according to claim 7;
   (b) cultivating the host cell under conditions supporting the production of a polypeptide encoded by the nucleic acid molecule; and
   (c) harvesting the polypeptide.

9. An isolated nucleic acid molecule consisting of a nucleic acid sequence selected from the group consisting of: Seq. I.D. No. 6, Seq. I.D. No. 9, Seq. I.D. No. 11, and Seq. I.D. No. 12.

10. A vector comprising a nucleic acid molecule according to claim 9.

11. An isolated host cell comprising a vector according to claim 10.

12. A method of producing a polypeptide, the method comprising:
   (a) providing an isolated host cell according to claim 11;
   (b) cultivating the host cell under conditions supporting the production of a polypeptide encoded by the nucleic acid molecule; and
   (c) harvesting the polypeptide.

* * * * *